(12) United States Patent
Hong et al.

(10) Patent No.: US 10,064,801 B2
(45) Date of Patent: Sep. 4, 2018

(54) RNA COMPLEXES THAT INHIBIT MELANIN PRODUCTION

(71) Applicant: OliX Pharmaceuticals, Inc., Seoul (KR)

(72) Inventors: Sun Woo Hong, Seoul (KR); Isu Hong, Seoul (KR); Ji Hyun Kim, Seoul (KR)

(73) Assignee: OliX Pharmaceuticals, Inc., Suwon-si (KR)

( * ) Notice: Subject to any disclaimer, the term of this patent is extended or adjusted under 35 U.S.C. 154(b) by 0 days.

(21) Appl. No.: 15/220,767

(22) Filed: Jul. 27, 2016

(65) Prior Publication Data

US 2017/0027837 A1 Feb. 2, 2017

Related U.S. Application Data

(60) Provisional application No. 62/197,370, filed on Jul. 27, 2015.

(51) Int. Cl.
| | | |
|---|---|---|
| *A61K 31/713* | (2006.01) | |
| *A61K 8/60* | (2006.01) | |
| *A61Q 19/02* | (2006.01) | |
| *C12N 15/113* | (2010.01) | |
| *A61K 45/06* | (2006.01) | |
| *A61Q 19/08* | (2006.01) | |

(52) U.S. Cl.
CPC ............ *A61K 8/606* (2013.01); *A61K 31/713* (2013.01); *A61K 45/06* (2013.01); *A61Q 19/02* (2013.01); *A61Q 19/08* (2013.01); *C12N 15/1137* (2013.01); *C12Y 114/18001* (2013.01); *A61K 2800/782* (2013.01); *C12N 2310/111* (2013.01); *C12N 2310/14* (2013.01); *C12N 2310/315* (2013.01); *C12N 2310/321* (2013.01); *C12N 2310/344* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 8,410,260 B2 * | 4/2013 | Collin-Djangone ... | A61K 8/606 424/450 |
| 8,822,428 B2 | 9/2014 | Collin-Djangone et al. | |
| 2013/0273657 A1 | 10/2013 | Lee | |

FOREIGN PATENT DOCUMENTS

| | | |
|---|---|---|
| CN | 102719432 A | 10/2012 |
| KR | 101207561 B1 | 12/2012 |

OTHER PUBLICATIONS

Chang, et al., "Asymmetric shorter-duplex siRNA structures trigger efficient gene silencing with reduced nonspecific effects," Mol Ther, 17(4): 725-732 (2009).
International Search Report and Written Opinion for International Application PCT/IB2016/001169, dated Oct. 26, 2016.
Jo, et al., "Selection and optimization of asymmetric siRNA targeting the human c-MET gene," Mol Cell, 32: 543-548 (2011).

* cited by examiner

*Primary Examiner* — Tracy Vivlemore
(74) *Attorney, Agent, or Firm* — Foley Hoag LLP; David P. Halstead; Brendan T. Jones

(57) ABSTRACT

In certain aspects, provided herein are RNA complexes (e.g., asymmetric RNA complexes, such as asiRNAs and lasiR-NAs) that inhibit tyrosinase expression and are therefore useful for reducing melanin production and for treating pigmentation-related disorders associated with excessive melanin production, such as melasma and age spots.

25 Claims, 15 Drawing Sheets
Specification includes a Sequence Listing.

Figure 5
(a)
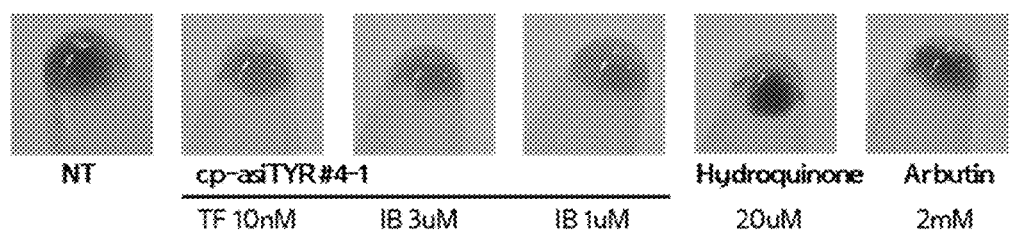
(b)
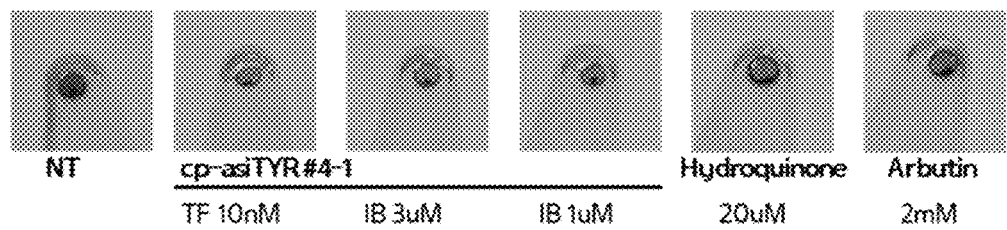

Figure 13

Human Tyrosinase mRNA sequence.

```
   1  atcactgtag tagtagctgg aaagagaaat ctgtgactcc aattagccag ttcctgcaga
  61  ccttgtgagg actagaggaa gaatgctcct ggctgttttg tactgcctgc tgtggagttt
 121  ccagacctcc gctggccatt tccctagagc ctgtgtctcc tctaagaacc tgatggagaa
 181  ggaatgctgt ccaccgtgga gcggggacag gagtccctgt ggccagcttt caggcagagg
 241  ttcctgtcag aatatccttc tgtccaatgc accacttggg cctcaatttc ccttcacagg
 301  ggtggatgac cgggagtcgt ggccttccgt cttttataat aggacctgcc agtgctctgg
 361  caacttcatg ggattcaact gtggaaactg caagtttggc ttttggggac caaactgcac
 421  agagagacga ctcttggtga gaagaaacat cttcgatttg agtgccccag agaaggacaa
 481  atttttttgcc tacctcactt tagcaaagca taccatcagc tcagactatg tcatccccat
 541  agggacctat ggccaaatga aaaatggatc aacacccatg tttaacgaca tcaatattta
 601  tgacctcttt gtctggatgc attattatgt gtcaatggat gcactgcttg ggggatctga
 661  aatctggaga gacattgatt ttgcccatga agcaccagct tttctgcctt ggcatagact
 721  cttcttgttg cggtgggaac aagaaatcca gaagctgaca ggagatgaaa acttcactat
 781  tccatattgg gactggcggg atgcagaaaa gtgtgacatt tgcacagatg agtacatggg
 841  aggtcagcac cccacaaatc ctaacttact cagcccagca tcattcttct cctcttggca
 901  gattgtctgt agccgattgg aggagtacaa cagccatcag tctttatgca atggaacgcc
 961  cgagggacct ttacggcgta atcctggaaa ccatgacaaa tccagaaccc caaggctccc
1021  ctcttcagct gatgtagaat tttgcctgag tttgacccaa tatgaatctg gttccatgga
1081  taaagctgcc aatttcagct ttagaaatac actggaagga tttgctagtc cacttactgg
1141  gatagcggat gcctctcaaa gcagcatgca caatgccttg cacatctata tgaatggaac
1201  aatgtccag gtacagggat ctgccaacga tcctatcttc cttcttcacc atgcatttgt
1261  tgacagtatt tttgagcagt ggctccgaag gcaccgtcct cttcaagaag tttatccaga
1321  agccaatgca cccattggac ataaccggga atcctacatg gttccttta taccactgta
1381  cagaaatggt gatttcttta tttcatccaa agatctgggc tatgactata gctatctaca
1441  agattcagac ccagactctt tcaagactta cattaagtcc tatttggaac aagcgagtcg
1501  gatctggtca tggctccttg gggcggcgat ggtaggggcc gtcctcactg ccctgctggc
1561  agggcttgtg agcttgctgt gtcgtcacaa gagaaagcag cttcctgaag aaaagcagcc
1621  actcctcatg gagaaagagg attaccacag cttgtatcag agccattat aaaaggctta
1681  ggcaatagag tagggccaaa aagcctgacc tcactctaac tcaaagtaat gtccaggttc
1741  ccagagaata tctgctggta ttttctgta aagaccattt gcaaattgt aacctaatac
1801  aaagtgtagc cttcttccaa ctcaggtaga acacacctgt ctttgtcttg ctgttttcac
1861  tcagcccttt taacattttc ccctaagccc atatgtctaa ggaaaggatg ctatttggta
1921  atgaggaact gttatttgta tgtgaattaa agtgctctta ttttaaaaaa ttgaaataat
1981  tttgattttt gccttctgat tatttaaaga tctatatatg ttttattggc cccttcttta
2041  ttttaataaa acagtgagaa atctaaaaaa aaaaaaaaaa aa
```

Figure 14
(a)
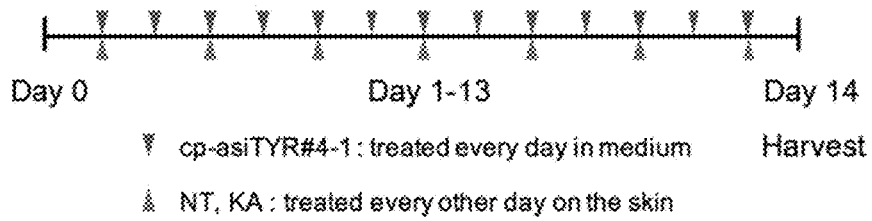
(b)
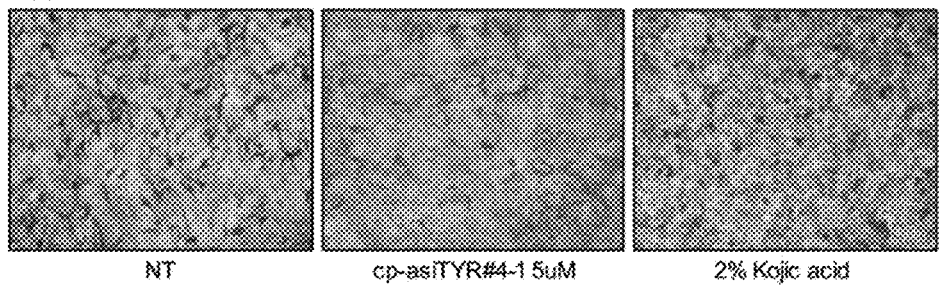
(c)
(d) 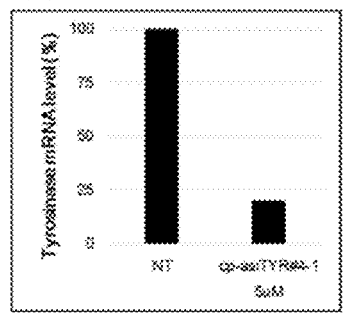 (e) 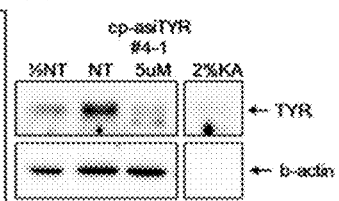 (f) 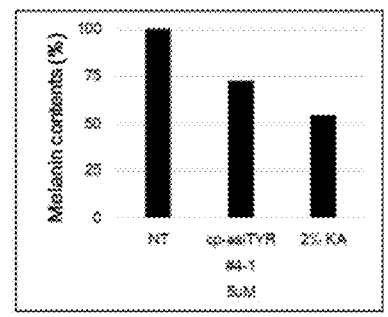

SEQUENCE LISTING

<160> NUMBER OF SEQ IDS NOS: 163

<210> SEQ ID NO 1
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cagggcuugu gagcuu                                                      16

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aagcucacaa gcccugccag c                                                21

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
auagaguagg gccaaa                                                      16

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uuuggcccua cucuauugcc u                                                21

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gaaauccaga agcuga                                                      16

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucagcuucug gauuucuugu u                                                21

```
<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcugacagga gaugaa                                                        16

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uucaucuccu gucagcuucu g                                                  21

<210> SEQ ID NO 9
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aacaagaaau ccagaa                                                        16

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uucuggauuu cuuguuccca c                                                  21

<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gauuggagga guacaa                                                        16

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uuguacuccu ccaaucggcu a                                                  21
```

<210> SEQ ID NO 13
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
acaagcgagu cggauc                                                     16

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gauccgacuc gcuuguucca a                                               21

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gccgauugga ggagua                                                     16

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uacuccucca aucggcuacu a                                               21

<210> SEQ ID NO 17
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ugaagcacca gcuuuu                                                     16

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaagcuggu gcuucauggg c                                               21

-continued

```
<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aaugaaaaau ggauca                                                      16

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugauccauuu uucauuuggc c                                                21

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
acaagaaauc cagaag                                                      16

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cuucuggauu ucuuguuccc a                                                21

<210> SEQ ID NO 23
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccgauuggag gaguac                                                      16

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
guacuccucc aaucggcuac a                                                21

<210> SEQ ID NO 25
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cagcugaugu agaauu                                                       16

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aauucuacau cagcugaaga g                                                 21

<210> SEQ ID NO 27
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cuggcgggau gcagaa                                                       16

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uucugcaucc cgccaguccc a                                                 21

<210> SEQ ID NO 29
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aggaguacaa cagcca                                                       16

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uggcuguugu acuccuccaa u                                                 21

<210> SEQ ID NO 31
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gcuaugacua uagcua                                                          16

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uagcuauagu cauagcccag a                                                    21

<210> SEQ ID NO 33
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cccauguuua acgaca                                                          16

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugucguuaaa caugguguu g                                                     21

<210> SEQ ID NO 35
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uagacucuuc uuguug                                                          16

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
caacaagaag agucuaugcc a                                                    21

<210> SEQ ID NO 37
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
cuguggaguu uccaga                                                      16

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucuggaaacu ccacagcagg c                                                21

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
caggcagagg uuccug                                                      16

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
caggaaccuc ugccugaaag c                                                21

<210> SEQ ID NO 41
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ggaccugcca gugcuc                                                      16

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gagcacuggc agguccuauu a                                                21

<210> SEQ ID NO 43
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
uacucagccc agcauc                                                        16

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaugcugggc ugaguaaguu a                                                  21

<210> SEQ ID NO 45
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ucagucuuua ugcaau                                                        16

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
auugcauaaa gacugauggc u                                                  21

<210> SEQ ID NO 47
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
acaagauuca gaccca                                                        16

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ugggucugaa ucuuguagau a                                                  21

<210> SEQ ID NO 49
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
caagcgaguc ggaucu                                                        16

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
agauccgacu cgcuuguucc a                                                  21

<210> SEQ ID NO 51
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaaaaggcuu aggcaa                                                        16

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uugccuaagc cuuuuauaaa u                                                  21

<210> SEQ ID NO 53
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cuauaugaau ggaaca                                                        16

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uguuccauuc auauagaugu g                                                  21

<210> SEQ ID NO 55
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 55
aagaucuggg cuauga                                          16

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ucauagccca gaucuuugga u                                    21

<210> SEQ ID NO 57
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
guccaaugca ccacuu                                          16

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
aaguggugca uuggacagaa g                                    21

<210> SEQ ID NO 59
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ucacaggggu ggauga                                          16

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ucauccaccc cugugaaggg a                                    21

<210> SEQ ID NO 61
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 61
ggccuuccgu cuuuua                                                    16

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uaaaagacgg aaggccacga c                                              21

<210> SEQ ID NO 63
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cugcaaguuu ggcuuu                                                    16

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
aaagccaaac uugcaguuuc c                                              21

<210> SEQ ID NO 65
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cagagaagga caaauu                                                    16

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
aauuuguccu ucucuggggc a                                              21

<210> SEQ ID NO 67
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 67
gcauaccauc agcuca                                                    16

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ugagcugaug guaugcuuug c                                              21

<210> SEQ ID NO 69
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69 uuggggauc ugaaau                                                     16

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
auuucagauc ccccaagcag u                                              21

<210> SEQ ID NO 71
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ucagcacccc acaaau                                                    16

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
auuugugggg ugcugaccuc c                                              21

<210> SEQ ID NO 73
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
```
gcccgaggga ccuuua                                                       16

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uaaagguccc ucgggcguuc c                                                 21

<210> SEQ ID NO 75
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ccauguuuaa cgacau                                                       16

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
augucguuaa acaugggugu u                                                 21

<210> SEQ ID NO 77
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ugacaggaga ugaaaa                                                       16

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuuucaucuc cugucagcuu c                                                 21

<210> SEQ ID NO 79
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79

```
caacuucaug ggauuc                                                          16

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gaaucccaug aaguugccag a                                                    21

<210> SEQ ID NO 81
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
guuccuguca gaauau                                                          16

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auauucugac aggaaccucu g                                                    21

<210> SEQ ID NO 83
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ccuauggcca aaugaa                                                          16

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uucauuuggc cauaggcccu                                                      21

<210> SEQ ID NO 85
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85 uuccgucag aauauc                                                           16
```

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gauauucuga caggaaccuc u                                              21

<210> SEQ ID NO 87
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
agguuccugu cagaau                                                    16

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
auucugacag gaaccucugc c                                              21

<210> SEQ ID NO 89
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggcaacuuca ugggau                                                    16

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
aucccaugaa guugccagag c                                              21

<210> SEQ ID NO 91
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
aacuucaugg gauuca                                                    16

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ugaaucccau gaaguugcca g                                                 21

<210> SEQ ID NO 93
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
accuauggcc aaauga                                                       16

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ucauuuggcc auaggucccu a                                                 21

<210> SEQ ID NO 95
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uauggccaaa ugaaaa                                                       16

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uuuucauuug gccauagguc c                                                 21

<210> SEQ ID NO 97
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cugacaggag augaaa                                                       16

```
<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uuucaucucc ugucagcuuc u                                              21

<210> SEQ ID NO 99
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
agcugacagg agauga                                                    16

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucaucuccug ucagcuucug g                                              21

<210> SEQ ID NO 101
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
acccauguuu aacgac                                                    16

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gucguuaaac augguguug a                                               21

<210> SEQ ID NO 103
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
aacacccaug uuuaac                                                    16

<210> SEQ ID NO 104
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
guuaaacaug gguguugauc c                                              21

<210> SEQ ID NO 105
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
cagucuuuau gcaaug                                                    16

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
cauugcauaa agacugaugg c                                              21

<210> SEQ ID NO 107
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aucagucuuu augcaa                                                    16

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uugcauaaag acugauggcu g                                              21

<210> SEQ ID NO 109
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
cuuggugaga agaaac                                                    16

<210> SEQ ID NO 110
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110 guucuucuc accaagaguc g                                                 21

<210> SEQ ID NO 111
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
cugccaacga uccuau                                                      16

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
auaggaucgu uggcagaucc c                                                21

<210> SEQ ID NO 113
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uccuacaugg uuccuu                                                      16

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
aaggaaccau guaggauucc c                                                21

<210> SEQ ID NO 115
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cuuugucugg augcau                                                      16

<210> SEQ ID NO 116
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 116
augcauccag acaaagaggu c                                            21

<210> SEQ ID NO 117
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
acauuugcac agauga                                                  16

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ucaucugugc aaaugucaca c                                            21

<210> SEQ ID NO 119
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gcggaugccu cucaaa                                                  16

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uuugagaggc auccgcuauc c                                            21

<210> SEQ ID NO 121
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
aaccgggaau ccuaca                                                  16

<210> SEQ ID NO 122
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 122
uguaggauuc ccgguuaugu c                                              21

<210> SEQ ID NO 123
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ggacauaacc gggaau                                                    16

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124 aucccgguu auguccaaug g                                               21

<210> SEQ ID NO 125
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gguuccuguc agaaua                                                    16

<210> SEQ ID NO 126
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uauucugaca ggaaccucug ccugaaagcu g                                   31

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ggatctggtc atggctcctt                                                20

<210> SEQ ID NO 128
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 128
gtcaggcttt ttggccctac                                                20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gagtcaacgg atttggtcgt                                                20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gacaagcttc ccgttctcag                                                20

<210> SEQ ID NO 131
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gcugacagga gaugaa                                                    16

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
uucaucuccu gucagcuucu g                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uucaucuccu gucagcuucu g                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 134
uucaucuccu gucagcuucu g                                              21

<210> SEQ ID NO 135
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gcugacagga gaugaa                                                    16

<210> SEQ ID NO 136
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ugaagcacca gcuuuu                                                    16

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
aaaagcuggu gcuucauggg c                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
aaaagcuggu gcuucauggg c                                              21

<210> SEQ ID NO 139
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugaagcacca gcuuuu                                                    16

<210> SEQ ID NO 140
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aaugaaaaau ggauca                                                    16

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ugauccauuu uucauuuggc c                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ugauccauuu uucauuuggc c                                              21

<210> SEQ ID NO 143
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
aaugaaaaau ggauca                                                    16

<210> SEQ ID NO 144
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cccauguuua acgaca                                                    16

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ugucguuaaa caugggeguu g                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 146
ugucguuaaa caugggnguuu g                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ugucguuaaa caugggnguuu g                                              21

<210> SEQ ID NO 148
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
cccauguuua acgaca                                                     16

<210> SEQ ID NO 149
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
agguuccugu cagaau                                                     16

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
auucugacag gaaccucugc c                                               21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
auucugacag gaaccucugc c                                               21

<210> SEQ ID NO 152
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
```

```
agguuccugu cagaau                                              16
```

<210> SEQ ID NO 153
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153

```
ggcaacuuca ugggau                                              16
```

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154

```
aucccaugaa guugccagag c                                        21
```

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155

```
aucccaugaa guugccagag c                                        21
```

<210> SEQ ID NO 156
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156

```
ggcaacuuca ugggau                                              16
```

<210> SEQ ID NO 157
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157

```
gcugacaggu cuacua                                              16
```

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uaguagaccu gucagcuucu g                                              21

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uucaucuccu gucagcuuc                                                 19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
uucaucuccu gucagcuuc                                                 19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uucaucuccu gucagcuuc                                                 19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uucaucuccu gucagcuuc                                                 19

<210> SEQ ID NO 163
<211> LENGTH: 2082
<212> TYPE: DNA
<213> ORGANISM: Homo sapiens

<400> SEQUENCE: 163
atcactgtag tagtagctgg aaagagaaat ctgtgactcc aattagccag ttcctgcaga     60
ccttgtgagg actagaggaa gaatgctcct ggctgttttg tactgcctgc tgtggagttt    120
ccagacctcc gctggccatt tccctagagc ctgtgtctcc tctaagaacc tgatggagaa    180
ggaatgctgt ccaccgtgga gcggggacag gagtccctgt ggccagcttt caggcagagg    240
ttcctgtcag aatatccttc tgtccaatgc accacttggg cctcaatttc ccttcacagg    300
ggtggatgac cgggagtcgt ggccttccgt cttttataat aggacctgcc agtgctctgg    360
caacttcatg ggattcaact gtggaaactg caagtttggc ttttgggac caaactgcac    420 agagagacga ctcttggtga aagaaacat cttcgatttg agtgcccag agaaggacaa    480 atttttgcc tacctcactt tagcaaagca taccatcagc tcagactatg tcatccccat    540

```
agggacctat ggccaaatga aaaatggatc aacacccatg tttaacgaca tcaatattta    600
tgacctcttt gtctggatgc attattatgt gtcaatggat gcactgcttg ggggatctga    660
aatctggaga gacattgatt ttgcccatga agcaccagct tttctgcctt ggcatagact    720
cttcttgttg cggtgggaac aagaaatcca gaagctgaca ggagatgaaa acttcactat    780
tccatattgg gactggcggg atgcagaaaa gtgtgacatt tgcacagatg agtacatggg    840
aggtcagcac cccacaaatc ctaacttact cagcccagca tcattcttct cctcttggca    900
gattgtctgt agccgattgg aggagtacaa cagccatcag tctttatgca atggaacgcc    960
cgagggacct ttacggcgta atcctggaaa ccatgacaaa tccagaaccc caaggctccc   1020
ctcttcagct gatgtagaat tttgcctgag tttgacccaa tatgaatctg gttccatgga   1080
taaagctgcc aatttcagct ttagaaatac actggaagga tttgctagtc cacttactgg   1140
gatagcggat gcctctcaaa gcagcatgca caatgccttg cacatctata tgaatggaac   1200
aatgtcccag gtacagggat ctgccaacga tcctatcttc cttcttcacc atgcatttgt   1260
tgacagtatt tttgagcagt ggctccgaag gcaccgtcct cttcaagaag tttatccaga   1320
agccaatgca cccattggac ataaccggga atcctacatg gttccttta taccactgta   1380 cagaaatggt gatttcttta tttcatccaa agatctgggc tatgactata gctatctaca   1440
agattcagac ccagactctt ttcaagacta cattaagtcc tatttggaac aagcgagtcg   1500
gatctggtca tggctccttg gggcggcgat ggtaggggcc gtcctcactg ccctgctggc   1560
agggcttgtg agcttgctgt gtcgtcacaa gagaaagcag cttcctgaag aaaagcagcc   1620
actcctcatg gagaaagagg attaccacag cttgtatcag agccatttat aaaaggctta   1680
ggcaatagag tagggccaaa aagcctgacc tcactctaac tcaaagtaat gtccaggttc   1740
ccagagaata tctgctggta ttttctgta aagaccattt gcaaaattgt aacctaatac   1800
aaagtgtagc cttcttccaa ctcaggtaga acacacctgt ctttgtcttg ctgttttcac   1860
tcagcccttt taacatttc ccctaagccc atatgtctaa ggaaaggatg ctatttggta   1920
atgaggaact gttatttgta tgtgaattaa agtgctctta ttttaaaaaa ttgaaataat   1980
tttgattttt gccttctgat tatttaaaga tctatatatg ttttattggc cccttcttta   2040
ttttaataaa acagtgagaa atctaaaaaa aaaaaaaaaa aa                      2082
```

RNA COMPLEXES THAT INHIBIT MELANIN PRODUCTION

RELATED APPLICATIONS

This application claims the benefit of U.S. provisional application 62/197,370, filed Jul. 27, 2015, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 6, 2016, is named OPH-00301_SL.txt and is 41,249 bytes in size.

BACKGROUND

Excess melanin production by melanocytes is associated with a variety of skin pigmentation-related disorders, including melasma and age spots. In melasma, excessive production of melanin results in black deposits in melanocytes present in the epidermal skin layer. Melasma is one of the leading refractory diseases occurring in the skin of women. Melasma often occurs in pregnant women and in women who are taking oral or patch contraceptives or undergoing hormone replacement therapy.

Tyrosinase is an oxidase that is the rate limiting enzyme in the synthesis of melanin and is therefore an important therapeutic target for agents that reduce hyperpigmentation and treat skin pigmentation-related disorders. In humans, the tyrosinase enzyme is encoded by the TYR gene. Mutations in the TYR gene that result in impaired tyrosinase production lead to type I oculocutaneous albinism.

Currently available treatments of skin pigmentation-related disorders associated with excessive melanin production include hydroquinone, arbutin, tretinoin, azelaic acid, kojic acid, chemical peels and microdermabrasion. However, such treatments are often ineffective and can have significant side-effects. Individuals with such disorders often need to resort to cosmetics to hide the areas of excessive skin pigmentation.

Thus, there is a need for improved compositions and methods for the inhibition of melanin production and the treatment of skin pigmentation-related disorders, including melasma and age spots.

SUMMARY

In certain aspects, provided herein are RNA complexes that inhibit tyrosinase and are useful for reducing melanin production and the treatment of pigmentation-related disorders, including melasma and age spots. In certain aspects, provided herein are pharmaceutical compositions comprising such RNA complexes and methods of using such RNA complexes and pharmaceutical compositions.

In certain aspects, provided herein is an RNA complex comprising an antisense strand having sequence complementarity to a tyrosinase mRNA sequence (e.g., a human tyrosinase mRNA sequence) and a sense strand having sequence complementarity to the antisense strand. In some embodiments, the RNA complex is capable of inhibiting tyrosinase expression by a cell (e.g., a melanocyte). In certain embodiments, the RNA complex is capable of inhibiting melanin production by a cell (e.g., a melanocyte). In some embodiments, the RNA complex is an asymmetric short interfering RNA (an asiRNA). In some embodiments, the RNA complex is a long asymmetric short interfering RNA (a lasiRNA). In some embodiments, the RNA complex is an RNA complex listed in Table 1, Table 2, Table 4, Table 5 and Table 6.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a cholesterol moiety. In some embodiments, the RNA complex is a modified RNA complex listed in Table 2 or Table 4. In certain embodiments, the RNA complex is not cytotoxic.

In certain aspects, provided herein is a pharmaceutical composition comprising an RNA complex provided herein and a pharmaceutically acceptable carrier. In certain embodiments, the pharmaceutical composition is formulated for topical delivery. In some embodiments, the pharmaceutical composition is a cream or a lotion. In some embodiments, the pharmaceutical composition further comprises a second skin lightening agent (e.g., hydroquinone, arbutin, tretinoin, kojic acid, azelaic acid or tranexamic acid).

In certain aspects, provided herein is a method of inhibiting tyrosinase expression by a cell (e.g., a melanocyte) comprising contacting the cell with an RNA complex provided herein. In certain aspects, provided herein is a method of inhibiting melanin production by a cell (e.g., a melanocyte) comprising contacting the cell with an RNA complex provided herein.

In certain aspects, provided herein is a method of inhibiting melanin production in the skin of a human subject comprising administering to the subject an RNA complex or pharmaceutical composition provided herein. In certain aspects, provided herein is a method of treating a human subject for a skin pigmentation disorder associated with excessive melanin production (e.g., melasma or age spots) comprising administering to the subject an RNA complex or pharmaceutical composition provided herein.

BRIEF DESCRIPTION OF THE DRAWINGS

FIG. 5 shows pigmentation inhibition by exemplary cp-asiRNAs. Panel (a) depicts the color change of MNT-1 cells 72 hours after treatment with cp-asiRNA without transfection vehicle. Panel (b) depicts the color change of the melanin obtained from the MNT-1 cell line 72 hours after treatment of the MNT-1 cells with cp-asiRNA without vehicle (NT=no treatment).

FIG. 13 provides the human tyrosinase mRNA sequence (SEQ ID NO: 163).

FIG. 14 shows inhibition of melanin synthesis in reconstructed skin model by an exemplary cp-asiRNA. Panel (a) depicts the experimental scheme for the study in which cp-MEL-300-B samples were treated every day for 13 days with asiTYR#4-1 in medium (13 times). Panel (b) shows light microscopy analysis of melanocyte in a no treatment control sample (NT), a cp-asiTYR#4-1 treated sample, and a kojic acid treated sample. Panel (c) shows Fontana-Massons staining for melanin analysis in a no treatment control sample (NT), a cp-asiTYR#4-1 treated sample, and a kojic acid treated sample. Panel (d) shows the tyrosinase mRNA level at day 14 as measured using real-time PCR. Panel (e) shows tyrosinase protein level at day 14 as measured by western blot. Panel (f) shows the melanin content of samples at day 14 as measured using a melanin contents assay.

DETAILED DESCRIPTION

General

Figure 1:
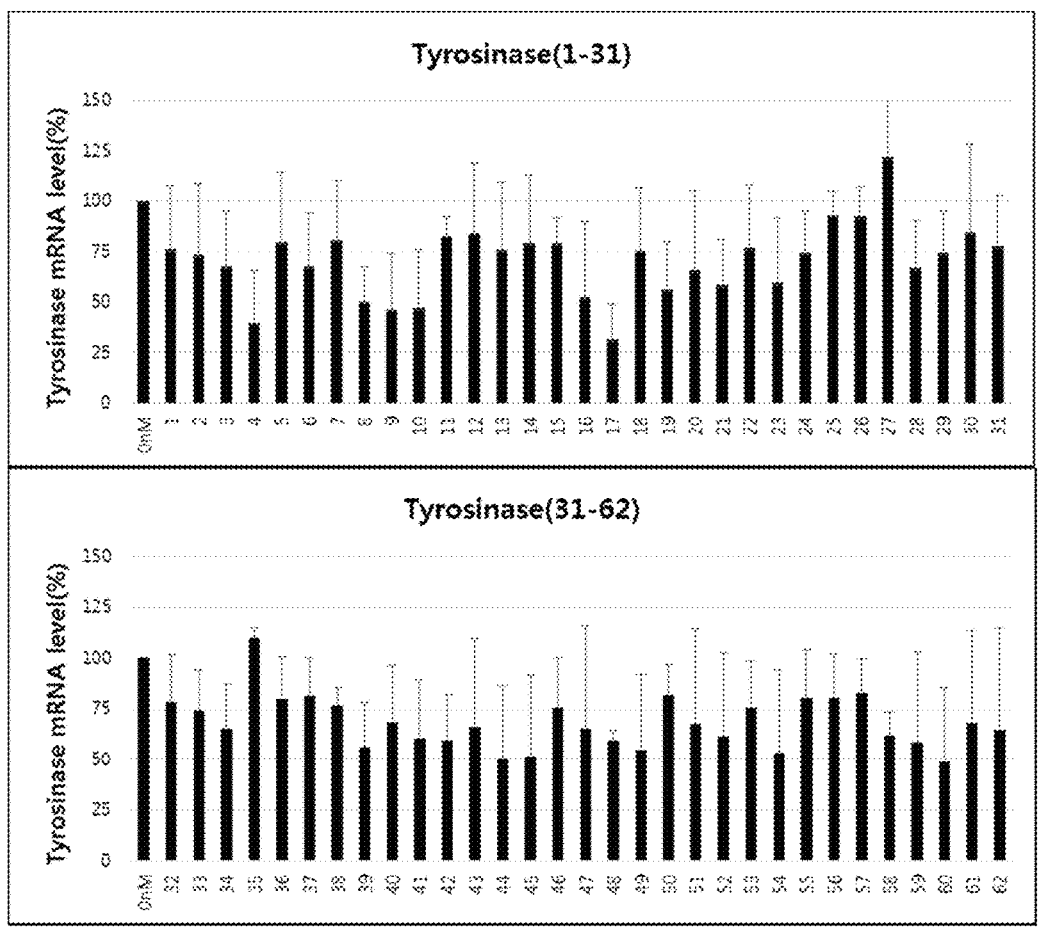
FIG. 1 shows the gene silencing efficiency of 62 exemplary asiRNAs that target tyrosinase. The asiRNAs were transfected in A375P at a concentration of 0.3 nM, and, after 24 hours, the degree of tyrosinase mRNA expression was measured using real-time PCR. The graph depicts the mean and standard deviation of three repeat experiments.

In certain aspects, provided herein are asymmetric RNA complexes (e.g., asiRNAs or lasiRNAs) that inhibit tyrosinase expression and are therefore useful for reducing melanin production and the treatment of pigmentation-related disorders associated with excessive melanin production, such as melasma and age spots. In some embodiments, the RNA complexes are chemically modified to be capable of penetrating a cell without need for a transfection vehicle. In some embodiments, the RNA complex is an RNA complex listed in Table 1, Table 2, Table 4, Table 5 and Table 6. In certain aspects, provided herein are pharmaceutical compositions comprising such RNA complexes and methods of using such RNA complexes and pharmaceutical compositions.

Tyrosinase is a protein that plays a key role in melanin synthesis. Various small molecule inhibitors targeting tyrosinase, including hydroquinone, retinoic acid and kojic acid, have been used as active ingredients of skin-whitening products. However, such treatments are often ineffective and often result in serious side effects, such as itching and skin browning.

In certain embodiments, the RNA complexes provided herein have reduced risk for side effects compared to the conventional small molecules currently in use for skin whitening. As described herein, exemplary RNA complexes provided herein have significant tyrosinase inhibitory effect, even at a 1000-fold lower concentration than current skin-whitening agents. Thus, the RNA complexes provided herein can replace or supplement currently available small molecule products for improved skin-whitening effects.

In some embodiments, the RNA complexes described herein are asiRNAs or lasiRNAs. As used herein, the term asiRNA refers to double-stranded asymmetrical short interfering RNA molecules that have a 19-21 nt antisense strand and a 13-17 nt sense strand. Additional information on asiRNAs can be found in U.S. Pat. Pub. No. 2012/0238017 and in Chang et al., *Mol. Ther.* 17:725-732 (2009), each of which is hereby incorporated by reference in its entirety. As used herein, the term lasiRNA refers to double-stranded long asymmetrical interfering RNA molecules that have a 13-21 nt sense strand and an antisense strand of greater than 24 nt. Additional information on lasiRNAs can be found in U.S. Pat. Pub. No. 2013/0273657, which is hereby incorporated by reference in its entirety.

In some embodiments, the RNA complexes described herein are delivered to cells using a delivery vehicle, such as liposomes, cationic polymers, cell penetrating peptides (CPPs), protein transduction domains (PTDs), antibodies and/or aptamers. In some embodiments, the RNA complex described herein is chemically modified so as to not require the use of such delivery vehicles to mediate tyrosinase inhibition in a cell. Such RNA complexes are referred to herein as cell-penetrating asiRNAs (cp-asiRNAs) or cell-penetrating lasiRNAs (cp-lasiRNAs).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, the terms "interfering nucleic acid," "inhibiting nucleic acid" are used interchangeably. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, asiRNA molecules, lasiRNA molecules, single-stranded siRNA molecules, miRNA molecules and shRNA molecules. Such an interfering nucleic acids can be designed to block or inhibit translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a heteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "polynucleotide", and "nucleic acid" are used interchangeably. They refer to a polymeric form of nucleotides, whether deoxyribonucleotides, ribonucleotides, or analogs thereof, in any combination and of any length. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The phrase "pharmaceutically-acceptable carrier" as used herein means a pharmaceutically-acceptable material, composition or vehicle, such as a liquid or solid filler, diluent, excipient, or solvent encapsulating material.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

RNA Complexes

In certain aspects, provided herein are RNA complexes that target tyrosinase mRNA and inhibit tyrosinase expression by a cell. Tyrosinase is an oxidase that is the rate-limiting enzyme for controlling production of melanin. The nucleic acid sequence of human tyrosinase mRNA is available at NCBI accession numbers NM_000372 and is provided in FIG. 13.

In certain aspects, provided herein is an RNA complex comprising an antisense strand having sequence complementarity to a tyrosinase mRNA sequence (e.g., a human tyrosinase mRNA sequence) and a sense strand having sequence complementarity to the antisense strand. In some embodiments, the RNA complex is capable of inhibiting tyrosinase expression by a cell (e.g., a melanocyte). In certain embodiments, the RNA complex is capable of inhibiting melanin production by a cell (e.g., a melanocyte). In some embodiments, the RNA complex is an asymmetric short interfering RNA (an asiRNA). In some embodiments, the RNA complex is a long asymmetric short interfering RNA (a lasiRNA). In some embodiments, the RNA complex is an RNA complex listed in Table 1, Table 2, Table 4, Table 5 and Table 6. The RNA complexes described herein can contain RNA bases, non-RNA bases or a mixture of RNA bases and non-RNA bases. For example, certain RNA complexes provided herein can be primarily composed of RNA bases but also contain DNA bases or non-naturally occurring nucleotides.

In some embodiments, the antisense strand is at least 19 nucleotides (nt) in length. In some embodiments, the antisense strand is 19 to 21 nt in length (i.e., 19, 20 or 21 nt in length). In some embodiments, at least 13, 14, 15, 16, 17, 18, 19, 20 or 21 nt of the antisense strand are complementary to the tyrosinase mRNA sequence. Perfect complementarity is not necessary. In some embodiments, the antisense strand is perfectly complementary to the tyrosinase mRNA sequence.

In some embodiments, the antisense strand is at least 24 nt in length (e.g., at least 25 nt in length, at least 26 nt in length, at least 27 nt in length, at least 28 nt in length, at least 29 nt in length, at least 30 nt in length or at least 31 nt in length). In some embodiments, the antisense strand is no greater than 124 nt in length (e.g., no greater than 100 nt in length, no greater than 90 nt in length, no greater than 80 nt in length, no greater than 70 nt in length, no greater than 60 nt in length, no greater than 50 nt in length or no greater than 40 nt in length. In some embodiments, the antisense strand is 31 nt in length. In some embodiments, at least 16, 17, 18, 19, 20, 21, 22, 23, 24, 25, 26, 27, 29, 29, 30 or 31 nt of the antisense strand are complementary to the tyrosinase mRNA sequence. Perfect complementarity is not necessary. In some embodiments, the antisense strand is perfectly complementary to the tyrosinase mRNA sequence.

In some embodiments, the sense strand is 15 to 17 nt in length (i.e., 15 nt in length, 16 nt in length or 17 nt in length). In some embodiments, at least 15 nt, at least 16 nt or at least 17 nt of the sense strand are complementary to the sequence of the antisense strand. In some embodiments the sense strand is perfectly complementary to the sequence of the antisense strand.

In some embodiments, the antisense strand and the sense strand form a complex in which the 5' end of the antisense strand and the 3' end of the sense strand form a blunt end. In some embodiments, the antisense strand and the sense strand form a complex in which the 5' end of the antisense strand overhangs the 3' end of the sense strand (e.g., by 1, 2, 3, 4 or 5 nt). In some embodiments, the antisense strand and the sense strand form a complex in which the 5' end of the sense strand overhangs the 3' end of the antisense strand (e.g., by 1, 2, 3, 4 or 5 nt).

In some embodiments, the antisense strand and/or the sense strand of the RNA complex has a sense strand sequence and/or an antisense strand sequence selected from the sequences listed in Table 1, Table 2, Table 4, Table 5 and Table 6. In some embodiments, the sense strand has a sequence of SEQ ID NO: 1 and the antisense strand has a sequence of SEQ ID NO: 2. In some embodiments, the sense strand has a sequence of SEQ ID NO: 3 and the antisense strand has a sequence of SEQ ID NO: 4. In some embodiments, the sense strand has a sequence of SEQ ID NO: 5 and the antisense strand has a sequence of SEQ ID NO: 6. In some embodiments, the sense strand has a sequence of SEQ ID NO: 7 and the antisense strand has a sequence of SEQ ID NO: 8. In some embodiments, the sense strand has a sequence of SEQ ID NO: 9 and the antisense strand has a sequence of SEQ ID NO: 10. In some embodiments, the sense strand has a sequence of SEQ ID NO: 11 and the antisense strand has a sequence of SEQ ID NO: 12. In some embodiments, the sense strand has a sequence of SEQ ID NO: 13 and the antisense strand has a sequence of SEQ ID NO: 14. In some embodiments, the sense strand has a sequence of SEQ ID NO: 15 and the antisense strand has a sequence of SEQ ID NO: 16. In some embodiments, the sense strand has a sequence of SEQ ID NO: 17 and the antisense strand has a sequence of SEQ ID NO: 18. In some embodiments, the sense strand has a sequence of SEQ ID NO: 19 and the antisense strand has a sequence of SEQ ID NO: 20. In some embodiments, the sense strand has a sequence of SEQ ID NO: 21 and the antisense strand has a sequence of SEQ ID NO: 22. In some embodiments, the sense strand has a sequence of SEQ ID NO: 23 and the antisense strand has a sequence of SEQ ID NO: 24. In some embodiments, the sense strand has a sequence of SEQ ID NO: 25 and the antisense strand has a sequence of SEQ ID NO: 26. In some embodiments, the sense strand has a sequence of SEQ ID NO: 27 and the antisense strand has a sequence of SEQ ID NO: 28. In some embodiments, the sense strand has a sequence of SEQ ID NO: 29 and the antisense strand has a sequence of SEQ ID NO: 30. In some embodiments, the sense strand has a sequence of SEQ ID NO: 31 and the antisense strand has a sequence of SEQ ID NO: 32. In some embodiments, the sense strand has a sequence of SEQ ID NO: 33 and the antisense strand has a sequence of SEQ ID NO: 34. In some embodiments, the sense strand has a sequence of SEQ ID NO: 35 and the antisense strand has a sequence of SEQ ID NO: 36. In some embodiments, the sense strand has a sequence of SEQ ID NO: 37 and the antisense strand has a sequence of SEQ ID NO: 38. In some embodiments, the sense strand has a sequence of SEQ ID NO: 39 and the antisense strand has a sequence of SEQ ID NO: 40. In some embodiments, the sense strand has a sequence of SEQ ID NO: 41 and the antisense strand has a sequence of SEQ ID NO: 42. In some embodiments, the sense strand has a sequence of SEQ ID NO: 43 and the antisense strand has a sequence of SEQ ID NO: 44. In some embodiments, the sense strand has a sequence of SEQ ID NO: 45 and the antisense strand has a sequence of SEQ ID NO: 46. In some embodiments, the sense strand has a sequence of SEQ ID NO: 47 and the antisense strand has a sequence of SEQ ID NO: 48. In some embodiments, the sense strand has a sequence of SEQ ID NO: 49 and the antisense strand has a sequence of SEQ ID NO: 50. In some embodiments, the sense strand has a sequence of SEQ ID NO: 51 and the antisense strand has a sequence of SEQ ID NO: 2. In some embodiments, the sense strand has a sequence of SEQ ID NO: 53 and the antisense strand has a sequence of SEQ ID NO: 54. In some embodiments, the sense strand has a sequence of SEQ ID NO: 55 and the antisense strand has a sequence of SEQ ID NO: 56. In some embodiments, the sense strand has a sequence of SEQ ID NO: 57 and the antisense strand has a sequence of SEQ ID NO: 58. In some embodiments, the sense strand has a sequence of SEQ ID NO: 59 and the antisense strand has a sequence of SEQ ID NO: 60. In some embodiments, the sense strand has a sequence of SEQ ID NO: 61 and the antisense strand has a sequence of SEQ ID NO: 62. In some embodiments, the sense strand has a sequence of SEQ ID NO: 63 and the antisense strand has a sequence of SEQ ID NO: 64. In some embodiments, the sense strand has a sequence of SEQ ID NO: 65 and the antisense strand has a sequence of SEQ ID NO: 66. In some embodiments, the sense strand has a sequence of SEQ ID NO: 67 and the antisense strand has a sequence of SEQ ID NO: 68. In some embodiments, the sense strand has a sequence of SEQ ID NO: 69 and the antisense strand has a sequence of SEQ ID NO: 70. In some embodiments, the sense strand has a sequence of SEQ ID NO: 71 and the antisense strand has a sequence of SEQ ID NO: 72. In some embodiments, the sense strand has a sequence of SEQ ID NO: 73 and the antisense strand has a sequence of SEQ ID NO: 74. In some embodiments, the sense strand has a sequence of SEQ ID NO: 75 and the antisense strand has a sequence of SEQ ID NO: 76. In some embodiments, the sense strand has a sequence of SEQ ID NO: 77 and the antisense strand has a sequence of SEQ ID NO: 78. In some embodiments, the sense strand has a sequence of SEQ ID NO: 79 and the antisense strand has a sequence of SEQ ID NO: 80. In some embodiments, the sense strand has a sequence of SEQ ID NO: 81 and the antisense strand has a sequence of SEQ ID NO: 82. In some embodiments, the sense strand has a sequence of SEQ ID NO: 83 and the antisense strand has a sequence of SEQ ID NO: 84. In some embodiments, the sense strand has a sequence of SEQ ID NO: 85 and the antisense strand has a sequence of SEQ ID NO: 86. In some embodiments, the sense strand has a sequence of SEQ ID NO: 87 and the antisense strand has a sequence of SEQ ID NO: 88. In some embodiments, the sense strand has a sequence of SEQ ID NO: 89 and the antisense strand has a sequence of SEQ ID NO: 90. In some embodiments, the sense strand has a sequence of SEQ ID NO: 91 and the antisense strand has a sequence of SEQ ID NO: 92. In some embodiments, the sense strand has a sequence of SEQ ID NO: 93 and the antisense strand has a sequence of SEQ ID NO: 94. In some embodiments, the sense strand has a sequence of SEQ ID NO: 95 and the antisense strand has a sequence of SEQ ID NO: 96. In some embodiments, the sense strand has a sequence of SEQ ID NO: 97 and the antisense strand has a sequence of SEQ ID NO: 98. In some embodiments, the sense strand has a sequence of SEQ ID NO: 99 and the antisense strand has a sequence of SEQ ID NO: 100. In some embodiments, the sense strand has a sequence of SEQ ID NO: 101 and the antisense strand has a sequence of SEQ ID NO: 102. In some embodiments, the sense strand has a sequence of SEQ ID NO: 103 and the antisense strand has a sequence of SEQ ID NO: 104. In some embodiments, the sense strand has a sequence of SEQ ID NO: 105 and the antisense strand has a sequence of SEQ ID NO: 106. In some embodiments, the sense strand has a sequence of SEQ ID NO: 107 and the antisense strand has a sequence of SEQ ID NO: 108. In some embodiments, the sense strand has a sequence of SEQ ID NO: 109 and the antisense strand has a sequence of SEQ ID NO: 110. In some embodiments, the sense strand has a sequence of SEQ ID NO: 111 and the antisense strand has a sequence of SEQ ID NO: 112. In some embodiments, the sense strand has a sequence of SEQ ID NO: 113 and the antisense strand has a sequence of SEQ ID NO: 114. In some embodiments, the sense strand has a sequence of SEQ ID NO: 115 and the antisense strand has a sequence of SEQ ID NO: 116. In some embodiments, the sense strand has a sequence of SEQ ID NO: 117 and the antisense strand has a sequence of SEQ ID NO: 118. In some embodiments, the sense strand has a sequence of SEQ ID NO: 119 and the antisense strand has a sequence of SEQ ID NO: 120. In some embodiments, the sense strand has a sequence of SEQ ID NO: 121 and the antisense strand has a sequence of SEQ ID NO: 122. In some embodiments, the sense strand has a sequence of SEQ ID NO: 123 and the antisense strand has a sequence of SEQ ID NO: 124. In some embodiments, the sense strand has a sequence of SEQ ID NO: 125 and the antisense strand has a sequence of SEQ ID NO: 126.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a cholesterol moiety. In some embodiments, the RNA complex is a modified RNA complex listed in Table 2 or Table 4. In certain embodiments, the RNA complex is not cytotoxic.

The RNA complexes described herein can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, each of which is hereby incorporated by reference in its entirety.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition. The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., *Science*, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C3-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., *Chemical Communications* (1998) 455; *Tetrahedron* (1998) 54:3607, and *Accounts of Chem. Research* (1999) 32:301); Obika, et al., *Tetrahedron Letters* (1997) 38:8735; (1998) 39:5401, and *Bioorganic Medicinal Chemistry* (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA-containing compound where each LNA subunit is separated by a DNA subunit. Certain compounds are composed of alternating LNA and DNA subunits where the intersubunit linker is phosphorothioate.

In certain embodiments, the RNA complex is linked to a cholesterol moiety. In some embodiments, the cholesterol moiety is attached to the 3' terminus of the sense strand. In some embodiments, the cholesterol moiety is attached to the 3' terminus of the antisense strand. In some embodiments, the cholesterol moiety is attached to the 5' terminus of the sense strand. In some embodiments, the cholesterol moiety is attached to the 5' terminus of the antisense strand.

In some embodiments, the RNA complex comprises a 2'-O-methylated nucleoside. 2'-O-methylated nucleosides carry a methyl group at the 2'-OH residue of the ribose molecule. 2'-O-Me-RNAs show the same (or similar) behavior as RNA, but are protected against nuclease degradation. 2'-O-Me-RNAs can also be combined with phosphothioate oligonucleotides (PTOs) for further stabilization. 2'-O-Me-RNAs (phosphodiester or phosphothioate) can be synthesized according to routine techniques in the art (see, e.g., Yoo et al., *Nucleic Acids Res.* 32:2008-16, 2004, which is hereby incorporated by reference).

In some embodiments, the 2'-O-methyl nucleoside is positioned at the 3' terminus of the sense strand. In some embodiments, 3' terminal region of the sense strand comprises a plurality of 2'-O-methylated nucleosides (e.g., 2, 3, 4, 5 or 6 2'-O-methylated nucleosides within 6 nucleosides of the 3' terminus). In some embodiments, the 2'-O-methyl nucleoside is positioned at the 3' terminus of the antisense strand. In some embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the 3' terminal region of the sense strand and the 3' terminal region of the antisense strand comprise a plurality of 2'-O-methylated nucleosides. In some embodiments, the sense strand comprises 2'-O-methylated nucleosides that alternate with unmodified nucleosides. In some embodiments, the sense strand comprises a contiguous sequence of 2, 3, 4, 5, 6, 7 or 8 2'-O-methylated nucleosides that alternate with unmodified nucleosides. In some embodiments, the anti-sense strand comprises 2'-O-methylated nucleosides that alternate with unmodified nucleosides. In some embodiments, the anti-sense strand comprises a contiguous sequence of 2, 3, 4, 5, 6, 7 or 8 2'-O-methylated nucleosides that alternate with unmodified nucleosides.

In some embodiments, the RNA complex comprises a phosphorothioate bond. "Phosphorothioates" (or S-oligos) are a variant of normal DNA in which one of the nonbridging oxygens is replaced by a sulfur. The sulfurization of the internucleotide bond reduces the action of endo- and exo-nucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-benzodithiol-3-one 1,1-dioxide (BDTD) (see, e.g., Iyer et al., *J. Org. Chem.* 55, 4693-4699, 1990). The latter methods avoid the problem of elemental sulfur's insolubility in most organic solvents and the toxicity of carbon disulfide. The TETD and BDTD methods also yield higher purity phosphorothioates.

In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some embodiments, all of the bonds between the ribonucleotides in the sense strand of the RNA complex are phosphorothioate bonds.

In some embodiments, at least 25%, 30%, 35%, 40%, 45%, 50%, 55%, 60%, 65%, 70%, 75%, 80%, 85%, 90% or 95% of the bonds between the ribonucleotides in the antisense strand of the RNA complex are phosphorothioate bonds. In some embodiments, all of the bonds between the ribonucleotides in the antisense strand of the RNA complex are phosphorothioate bonds.

The RNA complexes described herein may be contacted with a cell or administered to an organism (e.g., a human). Alternatively, constructs and/or vectors encoding the RNA complexes may be contacted with or introduced into a cell or organism. In certain embodiments, a viral, retroviral or lentiviral vector is used.

The RNA complexes described herein can be prepared by any appropriate method known in the art. For example, in some embodiments, the RNA complexes described herein are prepared by chemical synthesis or in vitro transcription.

Pharmaceutical Compositions

In certain aspects, provided herein is a pharmaceutical composition comprising an RNA complex provided herein and a pharmaceutically acceptable carrier. In certain embodiments, the pharmaceutical composition is formulated for topical delivery. In some embodiments, the pharmaceutical composition is a cream or a lotion. In some embodiments, the pharmaceutical composition further comprises a second skin lightening agent (e.g., hydroquinone, arbutin, tretinoin, kojic acid, azelaic acid or tranexamic acid). In certain embodiments, the pharmaceutical composition does not comprise a transfection vehicle. In some embodiments, the pharmaceutical composition comprises a delivery vehicle (e.g., liposomes, cationic polymers, cell penetrating peptides (CPPs), protein transduction domains (PTDs), antibodies and/or aptamers). In some embodiments, the composition includes a combination of multiple (e.g., two or more) of the RNA complexes described herein.

As described in detail below, the pharmaceutical compositions disclosed herein may be specially formulated for administration in solid or liquid form, including those adapted for topical administration (e.g., as a cream or lotion).

Methods of preparing these formulations or compositions include the step of bringing into association an RNA complex described herein with the carrier and, optionally, one or more accessory ingredients. In general, the formulations are prepared by uniformly and intimately bringing into association an agent described herein with liquid carriers.

The pharmaceutical compositions described herein can be provided in any cosmetically and/or dermatologically suitable form, for example, an emulsion, a cream, a mousse, a gel, a foam, a lotion, a mask, an ointment, a pomade, a solution, a serum, a spray, a stick, a patch, or a towelette. For example, pharmaceutical compositions for topical administration can be more or less fluid and have the appearance of a white or colored cream, of an ointment, of a milk, of a lotion, of a serum, of a paste, of a mousse or of a gel. It can, where appropriate, be applied to the skin in the form of an aerosol. It can also be present in solid form and, for example, be in the form of a stick. It can be used as a care product and/or as a skin makeup product.

In some embodiments, the pharmaceutical compositions described herein can, in addition to the RNA complex, contain at least one compound selected from: hydroquinone, arbutin, tretinoin, azelaic acid, tranexamic acid, α-hydroxyacids; salicylic acid and its derivatives such as n-octanoyl-5-salicylic acid; HEPES; procysteine; O-octanoyl-6-D-maltose; the disodium salt of methylglycinediacetic acid; ceramides; steroids such as diosgenin and derivatives of DHEA; kojic acid; N-ethyloxycarbonyl-4-paraaminophenol; ascorbic acid and its derivatives; bilberry extracts; retinoids and, in particular, retinol and its esters; polypeptides and their acylated derivatives; phytohormones; extracts of the yeast *Saccharomyces cerevisiae*; algal extracts; extracts of *Vitreoscilla filiformis*; extracts of soybean, lupin, corn and/or pea; alverine and its salts, in particular alverine citrate; resveratrol; carotenoids and, in particular, lycopene; tocopherol and its esters; coenzyme Q10 or ubiquinone;

xanthines and, in particular, caffeine and the natural extracts containing it; extracts of butcher's-broom and horse-chestnut; and their mixtures.

In some embodiments, the pharmaceutical compositions described herein can contain at least one UVA and/or UVB filter. The sunscreen filters can be selected from organic filters and inorganic filters and combinations thereof.

Examples of organic filters that block transmission of UV-A and/or the UV-B include: derivatives of paraminobenzoic acid (e.g., PABA, ethyl PABA, ethyldihydroxypropyl PABA, ethylhexyldimethyl PABA, glyceryl PABA, PEG-25 PABA), salicylic derivatives (e.g., homosalate, ethylhexyl salicylate, dipropyleneglycol salicylate, TEA salicylate) derivatives of dibenzoylmethane (e.g., butylmethoxydibenzoylmethane, isopropyldibenzoylmethane), cinnamic derivatives (e.g., ethylhexyl methoxycinnamate, isopropylmethoxycinnamate, isoamylmethoxycinnamate, cinoxate, DEA methoxycinnamate, diisopropyl methylcinnamate, glyceryl ethylhexanoate dimethoxycinnamate), derivatives of $\beta,\beta'$-diphenylacrylate (e.g., octocrylene, etocrylene), derivatives of benzophenone (e.g., benzophenone-1, benzophenone-2, benzophenone-3 or oxybenzone, benzophenone-4, benzophenone-5, benzophenone-6, benzophenone-8, benzophenone-9, and benzophenone-12), derivatives of benzylidene camphor (e.g., 3-benzylidene camphor, 4-methylbenzylidene camphor, benzylidene camphor sulfonic acid, camphor benzalkonium methosulfate, terephthalylidene dicamphor sulfonic acid and polyacrylamidomethyl benzylidene camphor), derivatives of phenyl benzimidazole (e.g., phenylbenzimidazole sulfonic acid, and benzimidazilate), derivatives of triazine (e.g., anisotriazine, ethylhexyl triazone, and diethylhexyl-butamidotriazone), derivatives of phenyl benzotriazole (e.g., drometrizole trisiloxane), anthranilic derivatives (menthyl anthranilate), imidazoline derivatives (e.g., ethylhexyldimethoxy-benzylidenedioxoimidazoline propionate), derivatives of benzalmalonate (polyorganosiloxane) and combinations thereof.

Examples of inorganic filters that block transmission of UV-A and/or the UV-B include: or uncoated metallic oxide nanopigments (mean size of the primary particles: in general, from 5 nm to 100 nm, preferably from 10 nm to 50 nm), such as nanopigments of titanium oxide (amorphous or crystallized in rutile and/or anatase form), of iron oxide, of zinc oxide, of zirconium oxide or of cerium oxide. Coating agents are, in addition, alumina and/or aluminum stearate.

In certain embodiments, the pharmaceutical compositions described herein also contain other cosmetic and dermatological ingredients, such as hydrophilic or lipophilic gelatinizing agents, preservatives, antioxidants, solvents, surfactants, thickeners, perfumes, fillers, pigments, odor absorbers and coloring substances.

In certain embodiments, the pharmaceutical compositions described herein also contain oils. Examples of oils that can be included in the pharmaceutical composition described herein include: hydrocarbonaceous oils of animal origin (e.g., perhydrosqualene), hydrocarbonaceous oils of vegetable origin (e.g., liquid fatty acid triglycerides which comprise from 4 to 10 carbon atoms and the liquid fraction of karite butter), synthetic esters and ethers of fatty acids (e.g., the oils of the formulae $R^1COOR^2$ and $R^1OR^2$ in which $R^1$ represents the residue of a fatty acid comprising from 8 to 29 carbon atoms and $R^2$ represents a branched or unbranched hydrocarbon chain which contains from 3 to 30 carbon atoms, such as Purcellin's oil, isononyl isononanoate, isopropyl myristate, ethyl-2-hexyl palmitate, octyl-2-dodecyl stearate, octyl-2-dodecyl erucate, and isostearyl isostearate; hydroxylated esters such as isostearyl lactate, octylhydroxystearate, octyldodecyl hydroxystearate, diisostearylmalate, triisocetyl citrate, and heptanoates, octanoates and decanoates of fatty alcohols; polyol esters, such as propylene glycol dioctanoate, neopentylglycol diheptanoate and diethyleneglycol diisononanoate; and pentaerythritol esters, such as pentaerythrityl tetraisostearate), linear or branched hydrocarbons of mineral or synthetic origin (e.g., volatile or nonvolatile paraffin oils and their derivatives, petrolatum, polydecenes, and hydrogenated polyisobutene such as parleam oil), fatty alcohols having from 8 to 26 carbon atoms (e.g., cetyl alcohol and stearyl alcohol and their mixture octyldodecanol, 2-butyloctanol, 2-hexyldecanol, 2-undecylpentadecanol, oleic alcohol or linoleic alcohol), partially hydrocarbonaceous and/or siliconaceous fluorinated oils, silicone oils (e.g., volatile or nonvolatile polymethylsiloxanes (PDMS) which have a linear or cyclic siliconaceous chain and which are liquid or pasty at ambient temperature, in particular cyclopoly-dimethylsiloxanes (cyclomethicones) such as cyclohexasiloxane; polydimethylsiloxanes which comprise alkyl, alkoxy or phenyl groups which are pendent or at the end of the siliconaceous chain, with the groups having from 2 to 24 carbon atoms; phenylated silicones such as phenyltrimethicones, phenyldimethicones, phenyl-trimethylsiloxydiphenylsiloxanes, diphenyldimethicones, diphenylmethyldiphenyltrisiloxanes, 2-phenylethyltrimethylsiloxysilicates and polymethylphenylsiloxanes), and combinations thereof.

Examples of emulsifiers and coemulsifiers which can be included in the pharmaceutical compositions described herein include O/W emulsifiers, such as esters of fatty acid and polyethylene glycol, in particular PEG-100 stearate, and esters of fatty acid and glycerol, such as glyceryl stearate, as well as W/O emulsifiers such as the oxyethylenated poly (methylcetyl)(dimethyl)-methylsiloxane or the mixture of ethylene glycol acetyl stearate and glyceryl tristearate.

Hydrophilic gelatinizing agents that can be included in the pharmaceutical compositions described herein include carboxyvinylic polymers (carbomer), acrylic polymers such as acrylate/alkyl acrylate copolymers, polyacrylamides, polysaccharides, natural gums and clays, while lipophilic gelatinizing agents which may be mentioned are modified clays such as bentonites, metallic salts of fatty acids, hydrophobic silica and polyethylenes.

Examples of fillers that may be included in the pharmaceutical compositions described herein include pigments, silica powder, talc, starch which is crosslinked with octenyl succinic anhydride, polyamide particles, polyethylene powders, microspheres based on acrylic copolymers, expanded powders such as hollow microspheres, silicone resin microbeads and combinations thereof.

In certain embodiments, the pharmaceutical compositions described herein are formulated for transdermal modes of delivery, such as patches and the like, with or without a suitable skin penetration enhancer. Accordingly, a transdermal means of delivering a composition or formulation (often with a skin penetration enhancer composition) to the skin is that of the transdermal patch or a similar device as known and described in the art. Examples of such devices are disclosed in U.S. Pat. Nos. 5,146,846, 5,223,262, 4,820,724, 4,379,454 and 4,956,171, each of which is hereby incorporated by reference. In some embodiments, the composition described herein is delivered by a microneedle patch. Exemplary microneedle patches are described in U.S. Pat. Nos. 5,697,901, 6,503,231, 6,611,707, 6,660,987, 8,162,901, 8,696,637 and 8,784,363, each of which is hereby incorporated by reference.

Therapeutic Methods

In certain aspects, provided herein is a method of inhibiting tyrosinase expression by a cell (e.g., a melanocyte) comprising contacting the cell with an RNA complex provided herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPPs), protein transduction domain (PTDs), antibody and/or aptamer). In some embodiments, the cell is present in the skin of a human subject. In some embodiments, the subject has a skin pigmentation disorder associated with excessive melanin production (e.g., melasma or age spots). In some embodiments, the subject is female. In some embodiments, the subject is pregnant or is taking oral or patch contraceptives or is undergoing hormone replacement therapy.

In certain aspects, provided herein is a method of inhibiting melanin production by a cell (e.g., a melanocyte) comprising contacting the cell with an RNA complex provided herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPPs), protein transduction domain (PTDs), antibody and/or aptamer). In some embodiments, the cell is present in the skin of a human subject. In some embodiments, the subject has a skin pigmentation disorder associated with excessive melanin production (e.g., melasma or age spots). In some embodiments, the subject is female. In some embodiments, the subject is pregnant or is taking oral or patch contraceptives or is undergoing hormone replacement therapy.

In certain aspects, provided herein is a method of inhibiting melanin production in the skin of a human subject comprising administering to the subject an RNA complex or pharmaceutical composition provided herein. In some embodiments, the subject has a skin pigmentation disorder associated with excessive melanin production (e.g., melasma or age spots). In some embodiments, the subject is female. In some embodiments, the subject is pregnant or is taking oral or patch contraceptives or is undergoing hormone replacement therapy. In certain embodiments, the RNA complex or pharmaceutical composition is administered topically to the skin of the subject. In some embodiments, the RNA complex or pharmaceutical composition is self-administered by the subject. In some embodiments, the method further comprises administering to the subject a second skin lightening agent (e.g., hydroquinone, arbutin, tretinoin, kojic acid, azelaic acid or tranexamic acid).

In certain aspects, provided herein is a method of treating a human subject for a skin pigmentation disorder associated with excessive melanin production (e.g., melasma or age spots) comprising administering to the subject an RNA complex or pharmaceutical composition provided herein. In some embodiments, the subject is female. In some embodiments, the subject is pregnant or is taking oral or patch contraceptives or is undergoing hormone replacement therapy. In certain embodiments, the RNA complex or pharmaceutical composition is administered topically to the skin of the subject. In some embodiments, the RNA complex or pharmaceutical composition self-administered by the subject. In some embodiments, the method further comprises administering to the subject a second skin lightening agent (e.g., hydroquinone, arbutin, tretinoin, kojic acid, azelaic acid or tranexamic acid).

In the present methods, an RNA complex described herein can be administered to the subject, for example, as nucleic acid without delivery vehicle (e.g., for cp-asiRNAs and cp-lasiRNAs), in combination with a delivery reagent, and/or as a nucleic acid comprising sequences that express the RNA complex described herein. In some embodiments, any nucleic acid delivery method known in the art can be used in the methods described herein. Suitable delivery reagents include, but are not limited to, e.g., the Minis Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. *Nucleic Acids Res.*, 32(13):e109 (2004); Hanai et al. *Ann NY Acad Sci.*, 1082:9-17 (2006); and Kawata et al. *Mol Cancer Ther* 7(9):2904-12 (2008); each of which is incorporated herein in their entirety. Exemplary interfering nucleic acid delivery systems are provided in U.S. Pat. Nos. 8,283,461, 8,313,772, 8,501,930, 8,426,554, 8,268,798 and 8,324,366, each of which is hereby incorporated by reference in its entirety.

In some embodiments of the methods described herein, liposomes are used to deliver an RNA complex described herein to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MIMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

The pharmaceutical compositions disclosed herein may be delivered by any suitable route of administration, including topically, orally and parenterally. In certain embodiments the pharmaceutical compositions are delivered generally (e.g., via oral or parenteral administration). In certain other embodiments the pharmaceutical compositions are delivered locally through direct administration to the skin.

Actual dosage levels of the RNA complexes in the pharmaceutical compositions may be varied so as to obtain an amount of RNA complex that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved. Similarly, an individual user could apply increasing amounts of the composition until the desired level of whitening is achieved.

In general, a suitable daily dose of an RNA complex described herein will be that amount of the RNA complex which is the lowest dose effective to produce a therapeutic effect. Such an effective dose will generally depend upon the factors described above.

EXEMPLIFICATION

Example 1: Screening for Tyrosinase-Specific Asymmetric Small Interfering RNAs

To identify asymmetric small interfering RNAs (asiR-NAs) that inhibit tyrosinase with high efficiency, 62 asiR-NAs were synthesized and screened. The nucleic acid sequences of the screened asiRNAs are provided in Table 1.

TABLE 1

Nucleic acid sequences for exemplary tyrosinase-targeting asiRNA.

| SEQ ID NO.: | SEQUENCE |
|---|---|
| 1 | asiTYR(1)S: CAGGGCUUGUGAGCUU |
| 2 | asiTYR(1)AS: AAGCUCACAAGCCCUGCCAGC |
| 3 | asiTYR(2)S: AUAGAGUAGGGCCAAA |
| 4 | asiTYR(2)AS: UUUGGCCCUACUCUAUUGCCU |
| 5 | asiTYR(3)S: GAAAUCCAGAAGCUGA |
| 6 | asiTYR(3)AS: UCAGCUUCUGGAUUUCUUGUU |
| 7 | asiTYR(4)S: GCUGACAGGAGAUGAA |
| 8 | asiTYR(4)AS: UUCAUCUCCUGUCAGCUUCUG |
| 9 | asiTYR(5)S: AACAAGAAAUCCAGAA |
| 10 | asiTYR(5)AS: UUCUGGAUUUCUUGUUCCCAC |
| 11 | asiTYR(6)S: GAUUGGAGGAGUACAA |
| 12 | asiTYR(6)AS: UUGUACUCCUCCAAUCGGCUA |
| 13 | asiTYR(7)S: ACAAGCGAGUCGGAUC |
| 14 | asiTYR(7)AS: GAUCCGACUCGCUUGUUCCAA |
| 15 | asiTYR(8)S: GCCGAUUGGAGGAGUA |
| 16 | asiTYR(8)AS: UACUCCUCCAAUCGGCUACUA |
| 17 | asiTYR(9)S: UGAAGCACCAGCUUUU |
| 18 | asiTYR(9)AS: AAAAGCUGGUGCUUCAUGGGC |
| 19 | asiTYR(10)S: AAUGAAAAAUGGAUCA |
| 20 | asiTYR(10)AS: UGAUCCAUUUUUCAUUUGGCC |
| 21 | asiTYR(11)S: ACAAGAAAUCCAGAAG |
| 22 | asiTYR(11)AS: CUUCUGGAUUUCUUGUUCCCA |
| 23 | asiTYR(12)S: CCGAUUGGAGGAGUAC |
| 24 | asiTYR(12)AS: GUACUCCUCCAAUCGGCUACA |
| 25 | asiTYR(13)S: CAGCUGAUGUAGAAUU |
| 26 | asiTYR(13)AS: AAUUCUACAUCAGCUGAAGAG |
| 27 | asiTYR(14)S: CUGGCGGGAUGCAGAA |
| 28 | asiTYR(14)AS: UUCUGCAUCCCGCCAGUCCCA |
| 29 | asiTYR(15)S: AGGAGUACAACAGCCA |
| 30 | asiTYR(15)AS: UGGCUGUUGUACUCCUCCAAU |
| 31 | asiTYR(16)S: GCUAUGACUAUAGCUA |
| 32 | asiTYR(16)AS: UAGCUAUAGUCAUAGCCCAGA |
| 33 | asiTYR(17)S: CC CAUGUUUAAC GACA |
| 34 | asiTYR(17)AS: UGUCGUUAAACAUGGGUGUUG |
| 35 | asiTYR(18)S: UAGACUCUUCUUGUUG |
| 36 | asiTYR(18)AS: CAACAAGAAGAGUCUAUGCCA |
| 37 | asiTYR(19)S: CUGUGGAGUUUCCAGA |
| 38 | asiTYR(19)AS: UCUGGAAACUCCACAGCAGGC |

TABLE 1-continued

Nucleic acid sequences for exemplary tyrosinase-targeting asiRNA.

| SEQ ID NO.: | SEQUENCE |
|---|---|
| 39 | asiTYR(20)S: CAGGCAGAGGUUCCUG |
| 40 | asiTYR(20)AS: CAGGAACCUCUGCCUGAAAGC |
| 41 | asiTYR(21)S: GGACCUGCCAGUGCUC |
| 42 | asiTYR(21)AS: GAGCACUGGCAGGUCCUAUUA |
| 43 | asiTYR(22)S: UACUCAGCCCAGCAUC |
| 44 | asiTYR(22)AS: GAUGCUGGGCUGAGUAAGUUA |
| 45 | asiTYR(23)S: UCAGUCUUUAUGCAAU |
| 46 | asiTYR(23)AS: AUUGCAUAAAGACUGAUGGCU |
| 47 | asiTYR(24)S: ACAAGAUUCAGACCCA |
| 48 | asiTYR(24)AS: UGGGUCUGAAUCUUGUAGAUA |
| 49 | asiTYR(25)S: CAAGCGAGUCGGAUCU |
| 50 | asiTYR(25)AS: AGAUCCGACUCGCUUGUUCCA |
| 51 | asiTYR(26)S: UAAAAGGCUUAGGCAA |
| 52 | asiTYR(26)AS: UUGCCUAAGCCUUUUAUAAAU |
| 53 | asiTYR(27)S: CUAUAUGAAUGGAACA |
| 54 | asiTYR(27)AS: UGUUCCAUUCAUAUAGAUGUG |
| 55 | asiTYR(28)S: AAGAUCUGGGCUAUGA |
| 56 | asiTYR(28)AS: UCAUAGCCCAGAUCUUUGGAU |
| 57 | asiTYR(29)S: GUCCAAUGCACCACUU |
| 58 | asiTYR(29)AS: AAGUGGUGCAUUGGACAGAAG |
| 59 | asiTYR(30)S: UCACAGGGGUGGAUGA |
| 60 | asiTYR(30)AS: UCAUCCACCCCUGUGAAGGGA |
| 61 | asiTYR(31)S: GGCCUUCCGUCUUUUA |
| 62 | asiTYR(31)AS: UAAAAGACGGAAGGCCACGAC |
| 63 | asiTYR(32)S: CUGCAAGUUUGGCUUU |
| 64 | asiTYR(32)AS: AAAGCCAAACUUGCAGUUCC |
| 65 | asiTYR(33)S: CAGAGAAGGACAAAUU |
| 66 | asiTYR(33)AS: AAUUUGUCCUUCUCUGGGCA |
| 67 | asiTYR(34)S: GCAUACCAUCAGCUCA |
| 68 | asiTYR(34)AS: UGAGCUGAUGGUAUGCUUUGC |
| 69 | asiTYR(35)S: UUGGGGGAUCUGAAAU |
| 70 | asiTYR(35)AS: AUUUCAGAUCCCCAAGCAGU |
| 71 | asiTYR(36)S: UCAGCACCCCACAAAU |
| 72 | asiTYR(36)AS: AUUUGUGGGGUGCUGACCUCC |
| 73 | asiTYR(37)S: GCCCGAGGGACCUUUA |
| 74 | asiTYR(37)AS: UAAAGGUCCCUCGGGCGUUCC |
| 75 | asiTYR(38)S: CCAUGUUUAACGACAU |
| 76 | asiTYR(38)AS: AUGUCGUUAAACAUGGGUGUU |
| 77 | asiTYR(39)S: UGACAGGAGAUGAAAA |
| 78 | asiTYR(39)AS: UUUUCAUCUCCUGUCAGCUUC |
| 79 | asiTYR(40)S: CAACUUCAUGGGAUUC |
| 80 | asiTYR(40)AS: GAAUCCCAUGAAGUUGCCAGA |
| 81 | asiTYR(41)S: GUUCCUGUCAGAAUAU |
| 82 | asiTYR(41)AS: AUAUUCUGACAGGAACCUCUG |
| 83 | asiTYR(42)S: CCUAUGGCCAAAUGAA |
| 84 | asiTYR(42)AS: UUCAUUUGGCCAUAGGUCCCU |
| 85 | asiTYR(43)S: UUCCUGUCAGAAUAUC |
| 86 | asiTYR(43)AS: GAUAUUCUGACAGGAACCUCU |
| 87 | asiTYR(44)S: AGGUUCCUGUCAGAAU |
| 88 | asiTYR(44)AS: AUUCUGACAGGAACCUCUGCC |
| 89 | asiTYR(45)S: GGCAACUUCAUGGGAU |
| 90 | asiTYR(45)AS: AUCCCAUGAAGUUGCCAGAGC |
| 91 | asiTYR(46)S: AACUUCAUGGGAUUCA |
| 92 | asiTYR(46)AS: UGAAUCCCAUGAAGUUGCCAG |
| 93 | asiTYR(47)S: ACCAUGGCCAAAUGA |
| 94 | asiTYR(47)AS: UCAUUUGGCCAUAGGUCCCUA |
| 95 | asiTYR(48)S: UAUGGCCAAAUGAAAA |
| 96 | asiTYR(48)AS: UUUUCAUUUGGCCAUAGGUCC |
| 97 | asiTYR(49)S: CUGACAGGAGAUGAAA |
| 98 | asiTYR(49)AS: UUUCAUCUCCUGUCAGCUUCU |
| 99 | asiTYR(50)S: AGCUGACAGGAGAUGA |
| 100 | asiTYR(50)AS: UCAUCUCCUGUCAGCUUCUGG |
| 101 | asiTYR(51)S: ACCCAUGUUUAACGAC |
| 102 | asiTYR(51)AS: GUCGUUAAACAUGGGUGUUGA |
| 103 | asiTYR(52)S: AACACCCAUGUUUAAC |
| 104 | asiTYR(52)AS: GUUAAACAUGGGUGUUGAUCC |
| 105 | asiTYR(53)S: CAGUCUUUAUGCAAUG |
| 106 | asiTYR(53)AS: CAUUGCAUAAAGACUGAUGGC |
| 107 | asiTYR(54)S: AUCAGUCUUUAUGCAA |
| 108 | asiTYR(54)AS: UUGCAUAAAGACUGAUGGCUG |
| 109 | asiTYR(55)S: CUUGGUGAGAAGAAAC |
| 110 | asiTYR(55)AS: GUUUCUUCUCACCAAGAGUCG |
| 111 | asiTYR(56)S: CUGCCAACGAUCCUAU |
| 112 | asiTYR(56)AS: AUAGGAUCGUUGGCAGAUCCC |
| 113 | asiTYR(57)S: UCCUACAUGGUUCCUU |

TABLE 1 -continued

Nucleic acid sequences for exemplary
tyrosinase-targeting asiRNA.

| SEQ ID NO.: | SEQUENCE | |
|---|---|---|
| 114 | asiTYR(57)AS: | AAGGAACCAUGUAGGAUUCCC |
| 115 | asiTYR(58)S: | CUUUGUCUGGAUGCAU |
| 116 | asiTYR(58)AS: | AUGCAUCCAGACAAAGAGGUC |
| 117 | asiTYR(59)S: | ACAUUUGCACAGAUGA |
| 118 | asiTYR(59)AS: | UCAUCUGUGCAAAUGUCACAC |
| 119 | asiTYR(60)S: | GCGGAUGCCUCUCAAA |
| 120 | asiTYR(60)AS: | UUUGAGAGGCAUCCGCUAUCC |
| 121 | asiTYR(61)S: | AACCGGGAAUCCUACA |
| 122 | asiTYR(61)AS: | UGUAGGAUUCCCGGUUAUGUC |
| 123 | asiTYR(62)S: | GGACAUAACCGGGAAU |
| 124 | asiTYR(62)AS: | AUUCCCGGUUAUGUCCAAUGG |

The asiRNAs listed in Table 1 were incubated at 95° C. for 2 minutes and at 37° C. for 1 hour in 1×siRNA duplex buffer (STpharm). Proper strand annealing was confirmed via gel electrophoresis. For the screen, 1.6×10⁴ A375 cells (ATCC) that had been cultured in Dulbecco's modified Eagle's medium (Gibco) containing 10% fetal bovine serum (Gibco) and 100 µg/ml penicillin/streptomycin in a 100 mm cell culture dish were seeded in 24-well plates. The A375 cells were transfected with 0.3 nM of the asiRNAs using Lipofectamine 2000 (Invitrogen) according to the manufacturer's instructions.

The tyrosinase mRNA levels in the transfected cells were measured 24 hours after transfection using real-time RTPCR. Specifically, total RNA were extracted using Isol-RNA lysis reagent (5PRIME), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the tyrosinase gene was detected using a power SYBR green PCR master Mix (Applied Biosystems). GAPDH was amplified as an internal control. The following primer sequences were used:

Human GAPDH-forward
    (SEQ ID NO: 129)
5'-GAG TCA ACG GAT TTG GTC GT-3'

Human GAPDH-reverse
    (SEQ ID NO: 130)
5'-GAC AAG CTT CCC GTT CTC AG-3'

Human Tyrosinase-forward:
    (SEQ ID NO: 127)
5'-GGA TCT GGT CAT GGC TCC TT-3'

Human Tyrosinase-reverse:
    (SEQ ID NO: 128)
5'-GTC AGG CTT TTT GGC CCT AC-3'

The level of tyrosinase inhibition by each of the 62 asiRNAs is provided in FIG. 1. Six of the asiRNA sequences, asiTYR(4), asiTYR(9), asiTYR(10), asiTYR (17), asiTYR(44) and asiTYR(45), were selected for use in follow-up studies.

Example 2: Chemical Modification of asiRNAs for Self-Delivery

Chemical modifications were applied to the six asiRNAs selected in Example 1 and the cellular delivery of the modified asiRNAs was tested in the absence of other delivery vehicle. As described below, certain of the modifications improved endocytosis and stability of the asiRNAs. Such cell penetrating asiRNAs (cp-asiRNAs) are able to be delivered into the cell in the absence of a delivery vehicle.

Thirty-eight potential cp-asiRNAs (Table 2) were screened for tyrosinase mRNA inhibition in MINT-1 cells. Each potential cp-asiRNA was incubated with MINT-1 cells, a human melanoma cell line, at 1 µM without a delivery vehicle and tyrosinase mRNA levels were measured by Real-Time PCR.

TABLE 2

Modified asiRNA sequences tested for self-delivery and tyrosinase inhibition.

| asiTYR(4)-1 S: | GCUGACAGGAGAUG*A*A*cholesterol | (SEQ ID NO: 131) |
|---|---|---|
| asiTYR(4)-1 AS: | UUCAUCUCCUGUCAGCU*U*C*U*G | (SEQ ID NO: 132) |
| asiTYR(4)-2 S: | GCUGACAGGAGAUG*A*A*cholesterol | (SEQ ID NO: 131) |
| asiTYR(4)-2 AS: | UUCAUCUCCUGUCAGCU*U*mC*mU*mG | (SEQ ID NO: 133) |
| asiTYR(4)-3 S: | GCUGACAGGAGAUG*A*A*cholesterol | (SEQ ID NO: 131) |
| asiTYR(4)-3 AS: | UUCAUCUCCUGUCAGCmU*mU*mC*mU*mG | (SEQ ID NO: 134) |
| asiTYR(4)-4 S: | mGCmUGmACmAGmGAmGAmUG*mA*A*cholesterol | (SEQ ID NO: 135) |
| asiTYR(4)-4 AS: | UUCAUCUCCUGUCAGCU*U*C*U*G | (SEQ ID NO: 132) |
| asiTYR(4)-5 S: | mGCmUGmACmAGmGAmGAmUG*mA*A*cholesterol | (SEQ ID NO: 135) |
| asiTYR(4)-5 AS: | UUCAUCUCCUGUCAGCU*U*mC*mU*mG | (SEQ ID NO: 133) |
| asiTYR(4)-6 S: | mGCmUGmACmAGmGAmGAmUG*mA*A*cholesterol | (SEQ ID NO: 135) |
| asiTYR(4)-6 AS: | UUCAUCUCCUGUCAGCmU*mU*mC*mU*mG | (SEQ ID NO: 134) |

TABLE 2-continued

Modified asiRNA sequences tested for self-delivery and tyrosinase inhibition.

| | | |
|---|---|---|
| asiTYR(9)-1 S: | UGAAGCACCAGCUU*U*U*cholesterol | (SEQ ID NO: 136) |
| asiTYR(9)-1 AS: | AAAAGCUGGUGCUUCAU*G*G*G*C | (SEQ ID NO: 137) |
| asiTYR(9)-3 S: | UGAAGCACCAGCUU*U*U*cholesterol | (SEQ ID NO: 136) |
| asiTYR(9)-3 AS: | AAAAGCUGGUGCUUCAmU*mG*mG*mG*mC | (SEQ ID NO: 138) |
| asiTYR(9)-4 S: | mUGmAAmGCmACmCAmGCmUU*mU*U*cholesterol | (SEQ ID NO: 139) |
| asiTYR(9)-4 AS: | AAAAGCUGGUGCUUCAU*G*G*G*C | (SEQ ID NO: 137) |
| asiTYR(9)-6 S: | mUGmAAmGCmACmCAmGCmUU*mU*U*cholesterol | (SEQ ID NO: 139) |
| asiTYR(9)-6 AS: | AAAAGCUGGUGCUUCAmU*mG*mG*mG*mC | (SEQ ID NO: 138) |
| asiTYR(10)-1 S: | AAUGAAAAAUGGAU*C*A*cholesterol | (SEQ ID NO: 140) |
| asiTYR(10)-1 AS: | UGAUCCAUUUUUCAUUU*G*G*C*C | (SEQ ID NO: 141) |
| asiTYR(10)-3 S: | AAUGAAAAAUGGAU*C*A*cholesterol | (SEQ ID NO: 140) |
| asiTYR(10)-3 AS: | UGAUCCAUUUUUCAUUmU*mG*mG*mC*mC | (SEQ ID NO: 142) |
| asiTYR(10)-4 S: | mAAmUGmAAmAAmAUmGGmAU*mC*A*cholesterol | (SEQ ID NO: 143) |
| asiTYR(10)-4 AS: | UGAUCCAUUUUUCAUUU*G*G*C*C | (SEQ ID NO: 141) |
| asiTYR(10)-6 S: | mAAmUGmAAmAAmAUmGGmAU*mC*A*cholesterol | (SEQ ID NO: 143) |
| asiTYR(10)-6 AS: | UGAUCCAUUUUUCAUUmU*mG*mG*mC*mC | (SEQ ID NO: 142) |
| asiTYR(17)-1 S: | CCCAUGUUUAACGA*C*A*cholesterol | (SEQ ID NO: 144) |
| asiTYR(17)-1 AS: | UGUCGUUAAACAUGGGU*G*U*U*G | (SEQ ID NO: 145) |
| asiTYR(17)-2 S: | CCCAUGUUUAACGA*C*A*cholesterol | (SEQ ID NO: 144) |
| asiTYR(17)-2 AS: | UGUCGUUAAACAUGGGU*G*mU*mU*mG | (SEQ ID NO: 146) |
| asiTYR(17)-3 S: | CCCAUGUUUAACGA*C*A*cholesterol | (SEQ ID NO: 144) |
| asiTYR(17)-3 AS: | UGUCGUUAAACAUGGGmU*mG*mU*mU*mG | (SEQ ID NO: 147) |
| asiTYR(17)-4 S: | mCCmCAmUGmUUmUAmACmGA*mC*A*cholesterol | (SEQ ID NO: 148) |
| asiTYR(17)-4 AS: | UGUCGUUAAACAUGGGU*G*U*U*G | (SEQ ID NO: 145) |
| asiTYR(17)-5 S: | mCCmCAmUGmUUmUAmACmGA*mC*A*cholesterol | (SEQ ID NO: 148) |
| asiTYR(17)-5 AS: | UGUCGUUAAACAUGGGU*G*mU*mU*mG | (SEQ ID NO: 146) |
| asiTYR(17)-6 S: | mCCmCAmUGmUUmUAmACmGA*mC*A*cholesterol | (SEQ ID NO: 148) |
| asiTYR(17)-6 AS: | UGUCGUUAAACAUGGGmU*mG*mU*mU*mG | (SEQ ID NO: 147) |
| asiTYR(44)-1 S: | AGGUUCCUGUCAGA*A*U*cholesterol | (SEQ ID NO: 149) |
| asiTYR(44)-1 AS: | AUUCUGACAGGAACCUC*U*G*C*C | (SEQ ID NO: 150) |
| asiTYR(44)-3 S: | AGGUUCCUGUCAGA*A*U*cholesterol | (SEQ ID NO: 149) |
| asiTYR(44)-3 AS: | AUUCUGACAGGAACCUmC*mU*mG*mC*mC | (SEQ ID NO: 151) |
| asiTYR(44)-4 S: | mAGmGUmUCmCUmGUmCAmGA*mA*U*cholesterol | (SEQ ID NO: 152) |
| asiTYR(44)-4 AS: | AUUCUGACAGGAACCUC*U*G*C*C | (SEQ ID NO: 150) |
| asiTYR(44)-6 S: | mAGmGUmUCmCUmGUmCAmGA*mA*U*cholesterol | (SEQ ID NO: 152) |
| asiTYR(44)-6 AS: | AUUCUGACAGGAACCUmC*mU*mG*mC*mC | (SEQ ID NO: 151) |
| asiTYR(45)-1 S: | GGCAACUUCAUGGG*A*U*cholesterol | (SEQ ID NO: 153) |
| asiTYR(45)-1 AS: | AUCCCAUGAAGUUGCCA*G*A*G*C | (SEQ ID NO: 154) |
| asiTYR(45)-3 S: | GGCAACUUCAUGGG*A*U*cholesterol | (SEQ ID NO: 153) |

TABLE 2-continued

Modified asiRNA sequences tested for self-delivery and tyrosinase inhibition.

| | | |
|---|---|---|
| asiTYR(45)-3 AS: | AUCCCAUGAAGUUGCCmA*mG*mA*mG*mC | (SEQ ID NO: 155) |
| asiTYR(45)-4 S: | mGGmCAmACmUUmCAmUGmGG*mA*U*cholesterol | (SEQ ID NO: 156) |
| asiTYR(45)-4 AS: | AUCCCAUGAAGUUGCCA*G*A*G*C | (SEQ ID NO: 154) |
| asiTYR(45)-6 S: | mGGmCAmACmUUmCAmUGmGG*mA*U*cholesterol | (SEQ ID NO: 156) |
| asiTYR(45)-6 AS: | AUCCCAUGAAGUUGCCmA*mG*mA*mG*mC | (SEQ ID NO: 155) | m = 2'-O-Methyl RNA.
* = phosphorothioate bond.

MNT-1 cells (obtained from Sungkyunkwan University) were cultured in Minimum Essential Media (Welgene) containing 20% fetal bovine serum (Gibco), 100 µg/ml penicillin/streptomycin, 10% 200 mM HEPES (Welgene) and 10% Dulbecco's modified Eagle's medium (Welgene).

The potential cp-asiRNAs listed in Table 2 were incubated at 95° C. for 2 minutes and at 37° C. for 1 hour in OPTI-MEM buffer (Gibco). Proper strand annealing of the potential cp-asiRNAs was confirmed by gel electrophoresis.

One day prior to cp-asiRNA treatment, $2.0 \times 10^4$ cells were seeded 24 well plates. Immediately before treatment, the MNT-1 cells were washed with 1×DPBS buffer (Gibco) then cultured in the presence of the potential cp-asiRNAs in OPTI-MEM buffer for 24 hours, at which point the asiRNA-containing OPTI-MEM media was replaced with a serum-containing media. Twenty-four hours later, tyrosinase mRNA levels were in the MNT-1 cells were determined.

Figure 2:
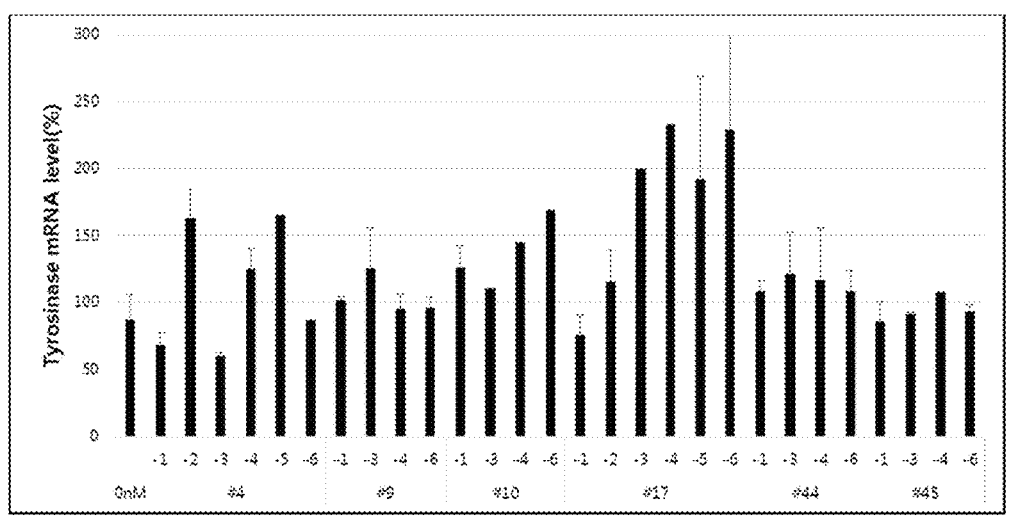
FIG. 2 shows the gene silencing efficiency of exemplary tyrosinase-targeting cell penetrating asiRNAs (cp-asiRNAs, or cp-asiTYRs) to which various chemical modifications have been applied. The cp-asiRNAs were incubated without transfection vehicle in the presence of MNT-1 cells at a concentration of 1 and, after 48 hours, the degree of tyrosinase mRNA expression was measured using real-time PCR. The graph depicts the mean and standard deviation of three repeat experiments.

The level of tyrosinase inhibition by each of the 38 potential cp-asiRNAs is provided in FIG. 2. From among the potential cp-asiRNAs tested, cp-asiTYR(4)-1 was selected for further study.

Example 3: Inhibition of Tyrosinase Protein and Melanin Using Tyrosine-Specific Cp-asiRNAs The efficacy of cp-asiTYR(4)-1 for the inhibition of tyrosinase protein and the suppression of melanin production was tested. To test for non-specific effects, a mutated cp-asiTYR that lacked sequence complementarity to the tyrosinase mRNA sequence (referred to as cp-asiTYR (seed mutation)) was also tested. The sequences of the cp-asiTYR (seed mutation) are provided in Table 3.

were seeded in 12-well plates. Immediately before treatment, the MNT-1 cells were washed with 1×DPBS buffer (Gibco), and then cultured in the presence of 1 µM or 3 µM of cp-asiRNATYR(4)-1 in OPTI-MEM buffer for 24 hours, at which point the OPTI-MEM media was replaced with a serum-containing media.

After 72 hours of cp-asiTYR(4)-1 incubation, the level of tyrosinase protein expression was determined via western blot. Briefly, the treated MNT-1 cells were lysed with RIPA buffer (GE). Fifteen µg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-tyrosinase antibody (Santa Cruz) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The tyrosinase and β-actin bands were then imaged using a Chemidoc instrument (Bio-rad).

Figure 3:
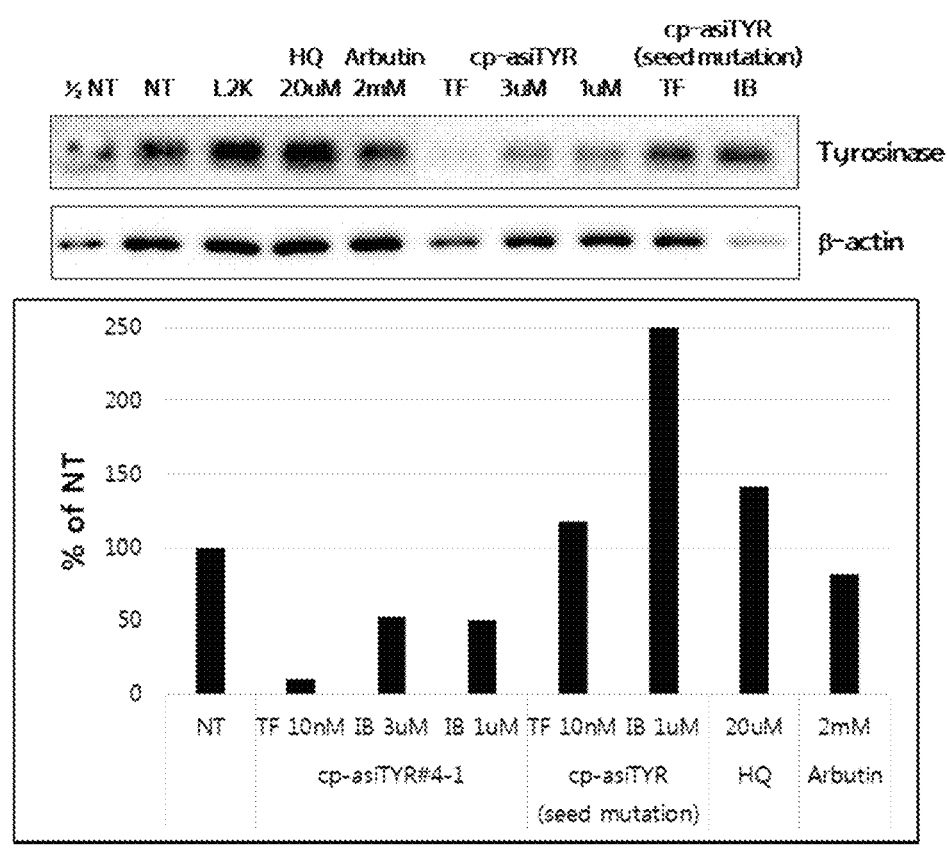
FIG. 3 shows the inhibition of tyrosinase protein expression by exemplary cp-asiRNAs. The cp-asiRNAs were contacted with MNT-1 cells without transfection vehicle and, after 72 hours, proteins were extracted and a western blot was performed (NT=no treatment).

The results of the western blot assay are depicted in FIG. 3. As a result, in all cp-asiTYR #4-1 incubated cell lines, 70% or more of tyrosinase protein inhibition were confirmed. In addition, the cp-asiTYR was shown to have a higher efficiency in the tyrosinase inhibition ability than other tyrosinase inhibitors such as Hydroquinone and Arbutin (FIG. 3).

TABLE 3

Sequences used in cp-asiRNA(4)-1 (seed mutation)

| | | |
|---|---|---|
| cp-asiTYR(4)-1(seed mutation) S: | GCUGACAGGUCUAC*U*A*chol. | (SEQ ID NO: 157) |
| cp-asiTYR(4)-1(seed mutation) AS: | UAGUAGACCUGUCAGCU*U*C*U*G | (SEQ ID NO: 158) | m = 2'-O-Methyl RNA.
* = phosphorothioate bond.

The cp-asiRNA was incubated at 95° C. for 2 minutes and at 37° C. for 1 hour in OPTI-MEM buffer (Gibco). Proper strand annealing of the potential cp-asiRNAs was confirmed by gel electrophoresis.

MNT-1 cells were cultured in Minimum Essential Media (Welgene) containing 20% fetal bovine serum (Gibco), 100 µg/ml penicillin/streptomycin, 10% 200 mM HEPES (Welgene) and 10% Dulbecco's modified Eagle's medium (Welgene). One day prior to treatment, $6.5 \times 10^4$ MNT-1 cells MNT-1 cells treated with cp-asiTYR(4)-1 as described above were tested for melanin content. After 72 hours of incubation in the presence of cp-asiTYR, the MNT-1 cells were collected, lysed with RIPA buffer (GE) and centrifuged at 13000 rpm. The resulting melanin pellet was dissolved in 100 µL of 1N NaOH (containing 10% DMSO) at 85° C. for 15 minutes and light absorption and melanin production were measured.

Figure 4:
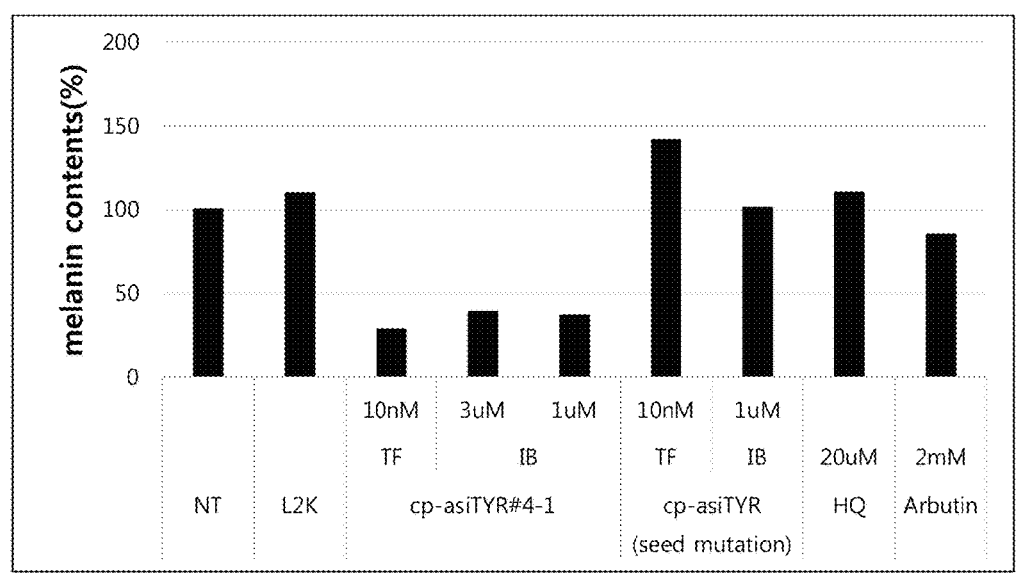
FIG. 4 shows the result of a melanin content assay performed 72 hours after the treatment of MNT-1 cells with exemplary cp-asiRNAs without transfection vehicle (NT=no treatment).

As shown in FIG. 4, MNT-1 cells treated with 1 µM cp-asiTYR(4)-1 showed greater than 60% inhibition in melanin production, which is higher than when treated with compounds commonly used for melanin production, including hydroquinone (20 µM) and arbutin (2 mM).

Example 4: MNT-1 Cell Lightening Following Treatment with Cp-asiRNAs

The ability of cp-asiRNA(4)-1 to lighten the color of MNT-1 cells was tested.

As in Example 3, MNT-1 cells were cultured in the presence of 1 µM or 3 µM cp-asiTYR(4)-1. After 72 hours, cells were pelleted and the color change of the cells was observed. As shown in FIG. 5, the color of the cp-asiTYR (4)-1 treated cells was lighter than untreated MNT-1 control cells (NT), hydroquinone treated cells and arbutin treated cells.

Example 5: Cytotoxicity of cp-asiRNAs

To test the cytotoxicity of cp-asiRNAs, MNT-1, a human melanoma cell line, and HaCaT, a human keratinocyte cell line were treated with cp-asiTYR #4-1 and hydroquinone.

The cp-asiRNA was incubated at 95° C. for 2 minutes and at 37° C. for 1 hour in OPTI-MEM buffer (Gibco). Proper strand annealing of the potential cp-asiRNAs was confirmed by gel electrophoresis.

One day before treatment with cp-asiRNA(4)-1, $5.0 \times 10^3$ MNT-1 cells or $1.0 \times 10^4$ HaCaT cells were seeded into 96 well plates. Immediately before treatment, the cells were washed with 1×DPBS buffer (Gibco), and then cultured in the presence of 1 µM or 3 µM of cp-asiRNATYR(4)-1 in OPTI-MEM buffer for 24 hours, at which point the cytotoxicity level was measured using a CytoTox96 Non-Radio Cytotoxicity assay (Promega) according to manufacturer's instructions. The media was then replaced with the serum-containing media and cell viability was measured using a cell counting kit-8 (Enzo) according to manufacturer's instructions.

Figure 6:
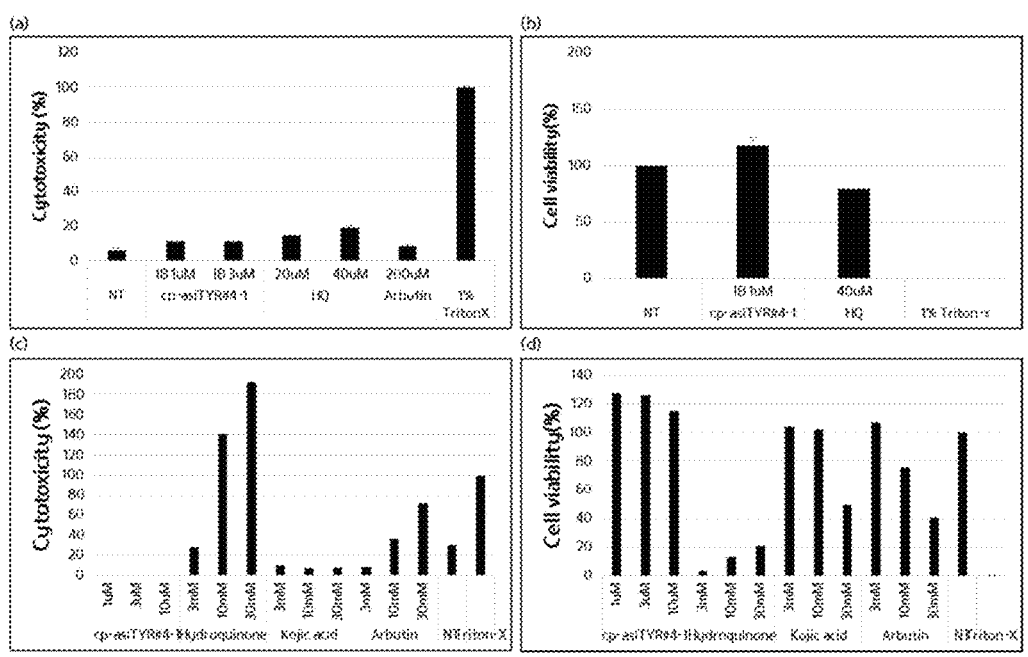
FIG. 6 shows the cytotoxicity of cells treated with exemplary cp-asiRNAs without transfection vehicle using a LDH assay and a CCK-8 assay. Panel (a) depicts the cytotoxicity in MNT-1 cells 24 hours after the treatment with the exemplary cp-asiRNAs or the indicated controls as determined by an LDH assay. Panel (b) depicts the cytotoxicity in MNT-1 cells 24 hours after the treatment with cp-asiRNAs or the indicated controls as determined by a CCK-8 assay. Panel (c) depicts the cytotoxicity in HaCaT cells 24 hours after treatment with cp-asiRNAs or controls as determined by an LDH assay. Panel (d) depicts the cytotoxicity of HaCaT cells 24 hours after treatment with cp-asiRNAs or controls as determined by a CCK-8 assay (NT=no treatment).

As shown in FIG. 6, no cytotoxicity or loss of cell viability was observed in either MNT-1 or HaCaT due to treatment with cp-asiRNA. On the other hand, cytotoxicity was observed in HaCaT cells treated with hydroquinone or arbutin.

Example 6: Additional cp-asiRNA Structures

A variety of potential cp-asiTYR structures having different strand lengths and numbers of 2'-O-methylation modifications were synthesized and tested for their ability to inhibit tyrosinase expression (Table 4).

TABLE 4

Additional cp-asiRNA sequences.

| | | |
|---|---|---|
| cp-asiTYR(4) S: | GCUGACAGGAGAUG*A*A*cholesterol | (SEQ ID NO: 131) |
| cp-asiTYR(4) 21AS-1: | UUCAUCUCCUGUCAGCU*U*C*U*G | (SEQ ID NO: 132) |
| cp-asiTYR(4) 21AS-2: | UUCAUCUCCUGUCAGCU*U*mC*mU*mG | (SEQ ID NO: 133) |
| cp-asiTYR(4) 21AS-3: | UUCAUCUCCUGUCAGCmU*mU*mC*mU*mG | (SEQ ID NO: 134) |
| cp-asiTYR(4) 19AS-4: | UUCAUCUCCUGUCAG*C*U*U*C | (SEQ ID NO: 159) |
| cp-asiTYR(4) 19AS-5: | UUCAUCUCCUGUCAG*C*mU*mU*mC | (SEQ ID NO: 160) |
| cp-asiTYR(4) 19AS-6: | UUCAUCUCCUGUCAmG*mC*mU*mU*mC | (SEQ ID NO: 161) | m = 2'-O-Methyl RNA.
* = phosphorothioate bond.

The ability of 1 µM of each of the potential cp-asiRNAs listed in Table 4 to inhibit tyrosinase mRNA in MNT-1 cells was tested.

MNT-1 cells were cultured in Minimum Essential Media (Welgene) containing 20% fetal bovine serum (Gibco), 100 µg/ml penicillin/streptomycin, 10% 200 mM HEPES (Welgene) and 10% Dulbecco's modified Eagle's medium (Welgene).

The potential cp-asiRNAs listed in Table 4 were incubated at 95° C. for 2 minutes and at 37° C. for 1 hour in OPTI-MEM buffer (Gibco). Proper strand annealing of the potential cp-asiRNAs was confirmed by gel electrophoresis.

One day prior to treatment, $2.0 \times 10^4$ MNT-1 cells were seeded in 24-well plates. Immediately before treatment, the MNT-1 cells were washed with 1×DPBS buffer (Gibco) then cultured in the presence of the potential cp-asiRNAs in OPTI-MEM buffer for 24 hours, at which point the asiRNA-containing OPTI-MEM media was replaced with a serum-containing media. Twenty-four hours later, tyrosinase mRNA levels were in the MNT-1 cells were determined.

Figure 7:
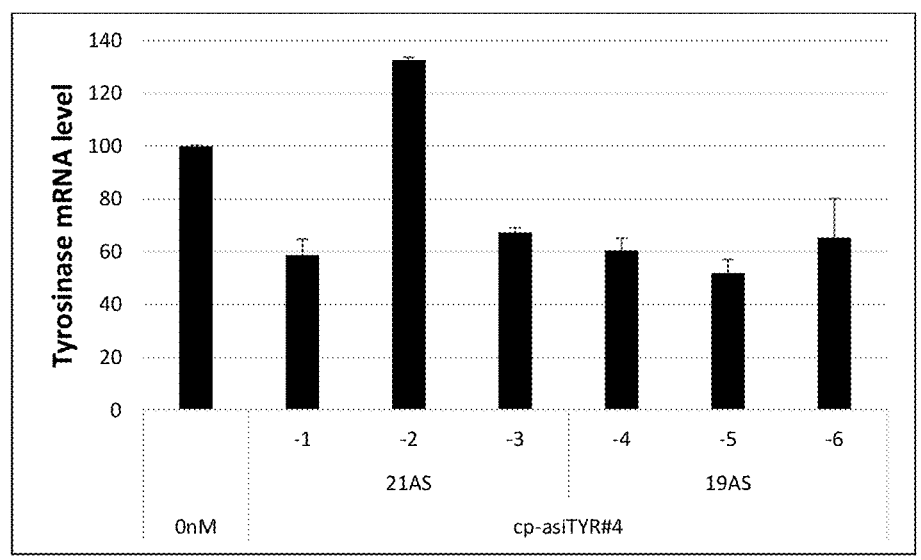
FIG. 7 shows the gene silencing effects of exemplary cp-asiRNAs of different antisense strand lengths (21 or 19 nucleotides) and containing 2'-O-Methylation modifications. Each cp-asiRNA was contacted to MNT-1 without transfection vehicle at 1 µM concentration and the resulting tyrosinase mRNA production was measured by Real-Time PCR after 48 hours.

As seen in FIG. 7, tyrosinase mRNA potential cp-asiR-NAs containing 4 phosphorothioate bonds on 21 nucleotide antisense strands and potential cp-asiRNAs containing three 2'-O-Methylation and four phosphorothioate bonds on 19 nucleotide antisense strands exhibited the highest levels of tyrosinase inhibition. The cp-asiTYR(4) 21AS-1 and cp-asiTYR(4) 19AS-5 were selected for further experimentation.

The effect of cp-asiTYR(4) 21AS-1 and cp-asiTYR(4) 19AS-5 on the production tyrosinase protein and melanin production was tested.

The cp-asiRNA was incubated at 95° C. for 2 minutes and at 37° C. for 1 hour in OPTI-MEM buffer (Gibco). Proper strand annealing of the potential cp-asiRNAs was confirmed by gel electrophoresis.

MNT-1 cells were cultured in Minimum Essential Media (Welgene) containing 20% fetal bovine serum (Gibco), 100 µg/ml penicillin/streptomycin, 10% 200 mM HEPES (Welgene) and 10% Dulbecco's modified Eagle's medium (Welgene). One day prior to treatment, $6.5 \times 10^4$ MNT-1 cells were seeded in 12-well plates. Immediately before treatment, the MNT-1 cells were washed with 1×DPBS buffer (Gibco), and then cultured in the presence of 1 µM or 3 µM of cp-asiRNATYR(4)-1 in OPTI-MEM buffer for 24 hours, at which point the OPTI-MEM media was replaced with a serum-containing media.

The level of tyrosinase protein expression by MNT-1 cells after treatment with 1 µM and 3 µM cp-asiRNAs was determined via western blot. Briefly, the transfected MNT-1 cells were lysed with RIPA buffer (GE). Fifteen µg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-tyrosinase antibody (Santa Cruz) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The tyrosinase and β-actin bands were then imaged using a Chemidoc instrument (Bio-rad).

Figure 8:
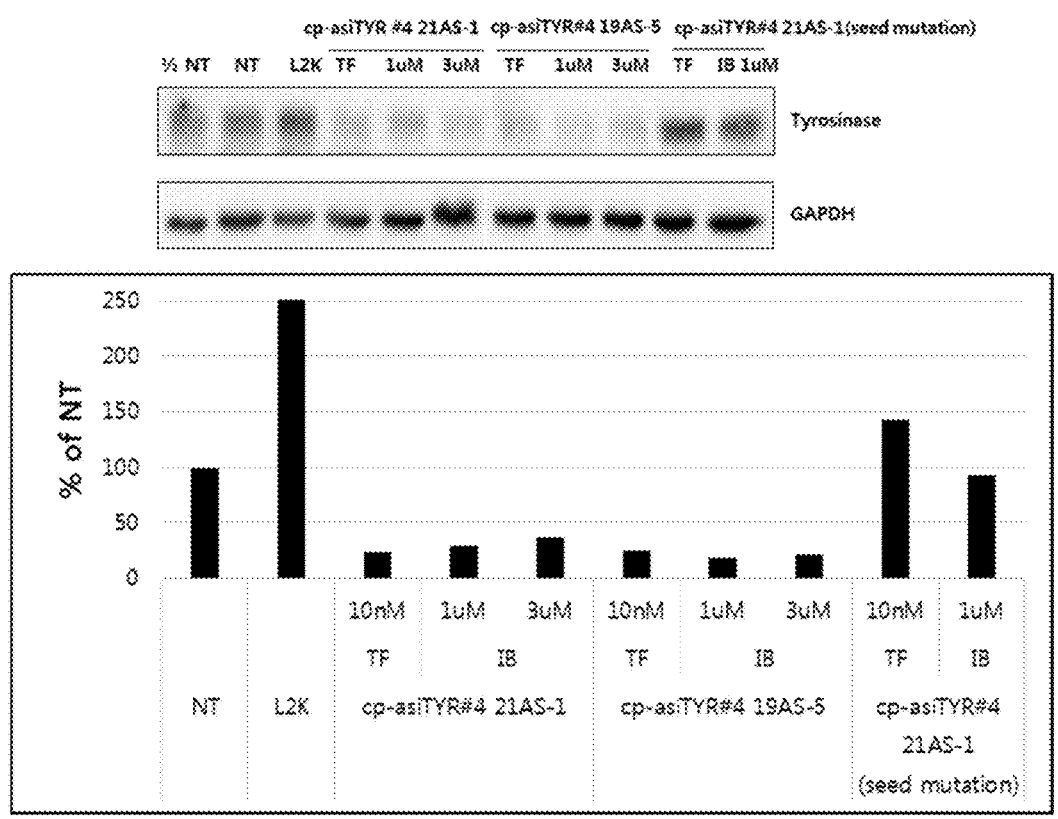
FIG. 8 shows the inhibition of tyrosinase protein expression by exemplary cp-asiRNAs. The indicated cp-asiRNAs were contacted to MNT-1 cells without transfection vehicle and, after 72 hours, proteins were extracted and a western blot was performed (NT=no treatment).

As seen in FIG. 8, treatment with cp-asiTYR(4) 21AS-1 or cp-asiTYR(4) 19AS-5 resulted in a greater than 70% inhibition in the level of tyrosinase protein. In addition, with cp-asiTYR(4) 19AS-5 exhibiting a slightly higher inhibitory activity than cp-asiTYR(4) 21AS-1.

MNT-1 cells treated with cp-asiTYR(4) 21AS-1 or cp-asiTYR(4) 19AS-5 as described above were tested for melanin content. After 72 hours of incubation in the presence of cp-asiTYR, the MNT-1 cells were collected, lysed with RIPA buffer (GE) and centrifuged at 13000 rpm. The resulting melanin pellet was dissolved in 100 µL of 1N NaOH (containing 10% DMSO) at 85° C. for 15 minutes and light absorption and melanin production were measured.

Figure 9:
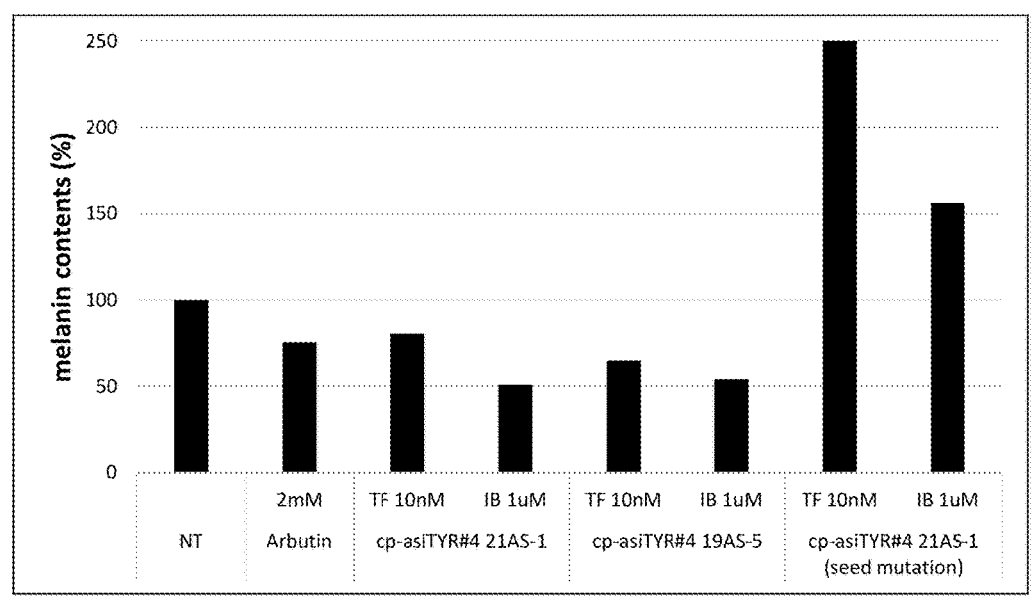
FIG. 9 shows the results produced by a melanin content assay performed 72 hours after the treatment of MNT-1 cells with exemplary cp-asiRNAs without transfection vehicle. (NT=no treatment).

As shown in FIG. 9, MNT-1 cells treated with 1 µM cp-asiTYR(4) 21AS-1 or cp-asiTYR(4) 19AS-5 showed about a 50% inhibition in melanin production, which is higher than the inhibition shown in MNT-1 cells treated with 2 mM arbutin.

Additional potential cp-asiTYR structures having different strand lengths, numbers of 2'-O-methylation modifications and numbers of phosphorothioate bond were synthesized and tested for their ability to inhibit tyrosinase expression (Table 5).

gene). One day prior to treatment, 6.5×10$^4$ MNT-1 cells were seeded in 12-well plates. Immediately before treatment, the MNT-1 cells were washed with 1×DPBS buffer (Gibco), and then cultured in the presence of 1 µM, 0.6 µM, 0.3 µM and 0.1 µM of cp-asiTYR(4) 21AS-1 and cp-asiTYR(4) 19AS-7 in OPTI-MEM buffer for 24 hours, at which point the OPTI-MEM media was replaced with a serum-containing media.

The level of tyrosinase protein expression by MNT-1 cells after treatment with 1 µM, 0.6 µM, 0.3 µM and 0.1 µM cp-asiRNAs was determined via western blot. Briefly, the transfected MNT-1 cells were lysed with RIPA buffer (GE). Fifteen of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-tyrosinase antibody (Santa Cruz) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The tyrosinase and β-actin bands were then imaged using a Chemidoc instrument (Bio-rad).

Figure 10:
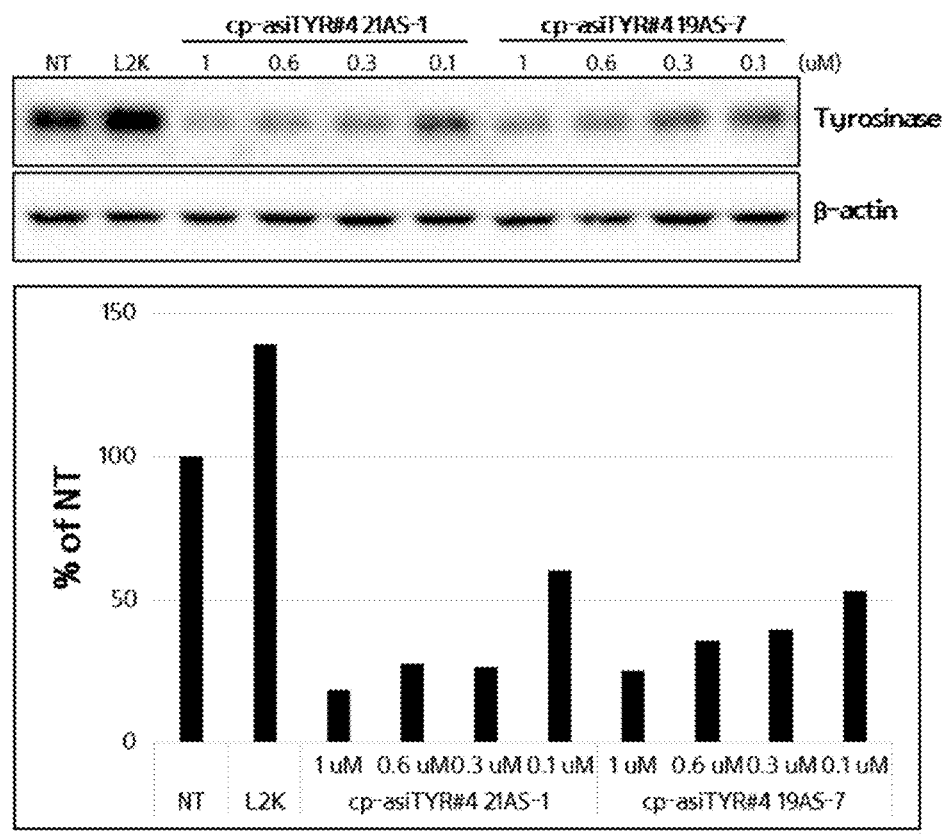
FIG. 10 shows the inhibition of tyrosinase protein expression by exemplary cp-asiRNAs. The indicated cp-asiRNAs were contacted to MNT-1 cells without transfection vehicle and, after 72 hours, proteins were extracted and a western blot was performed (NT=no treatment).

As seen in FIG. 10, treatment with cp-asiTYR(4) 21AS-1 or cp-asiTYR(4) 19AS-7 resulted in a greater than 70% inhibition in the level of tyrosinase protein. In addition, with cp-asiTYR(4) 21AS-1 exhibiting a slightly higher inhibitory activity than cp-asiTYR(4) 19AS-7.

Example 7: Use of Cell Penetrating Peptide with asiRNAs and lasiRNAs

The combination of asiRNAs or lasiRNA with Pepfect 6 (PF6) cell penetrating peptide was tested for inhibition of tyrosinase mRNA and protein level without use of another transfection reagent.

TABLE 5

Additional cp-asiRNA sequences.

| | | |
|---|---|---|
| cp-asiTYR(4) S: | GCUGACAGGAGAUG*A*A*cholesterol | (SEQ ID NO: 131) |
| cp-asiTYR(4) 21AS-1: | UUCAUCUCCUGUCAGCU*U*C*U*G | (SEQ ID NO: 132) |
| cp-asiTYR(4) 19AS-7: | UUCAUCUCCUGUC*A*G*C*mU*mU*mC | (SEQ ID NO: 162) | m = 2'-O-Methyl RNA.
* = phosphorothioate bond.

The effect of cp-asiTYR(4) 21AS-1 and cp-asiTYR(4) 19AS-7 on the tyrosinase protein production was tested.

The cp-asiRNA was incubated at 95° C. for 2 minutes and at 37° C. for 1 hour in OPTI-MEM buffer (Gibco). Proper strand annealing of the potential cp-asiRNAs was confirmed by gel electrophoresis.

MNT-1 cells were cultured in Minimum Essential Media (Welgene) containing 20% fetal bovine serum (Gibco), 100 µg/ml penicillin/streptomycin, 10% 200 mM HEPES (Welgene) and 10% Dulbecco's modified Eagle's medium (Welgene).

asiTYR(4) and lasiTYR(21) (Table 6) were incubated at 95° C. for 2 minutes and at 37° C. for 1 hour in OPTI-MEM buffer (Gibco). Proper strand annealing of the asiRNA and lasiRNA was confirmed by gel electrophoresis. Annealed RNA and PF6 in DEPC was diluted in 100 µl 0.6×DPBS with a molar ratio of RNA complex:PF6 of 1:10 and then incubated at room temperature for 30 minutes for complex formation. Proper complex formation was confirmed by gel electrophoresis.

TABLE 6

Nucleic acid sequence of asiTYR(4) and lasiTYR(21).

asiTYR(4)S: GCUGACAGGAGAUGAA (SEQ ID NO: 7)

asiTYR(4)AS: UUCAUCUCCUGUCAGCUUCUG (SEQ ID NO: 8)

lasiTYR(21)S: GGUUCCUGUCAGAAUA (SEQ ID NO: 125)

lasiTYR(21)AS: UAUUCUGACAGGAACCUCUGCCUGAAAGCUG (SEQ ID NO: 126)

MNT-1 cells were cultured in Minimum Essential Media (Welgene) containing 20% fetal bovine serum (Gibco), 100 μg/ml penicillin/streptomycin, 10% 200 mM HEPES (Welgene) and 10% Dulbecco's modified Eagle's medium (Welgene). One day prior to treatment, $6.5 \times 10^4$ MNT-1 cells were seeded in 12-well plates. Four hours prior to treatment, the cell media was replaced with 900 μL of FBS-containing media. The PF6-complexed asiRNA or lasiRNA was added to the cells and the cells were incubated for 24 hours, at which point the media was replaced. Tyrosinase mRNA levels were measured using real-time RT-PCR 24 hours after media replacement.

Figure 11:
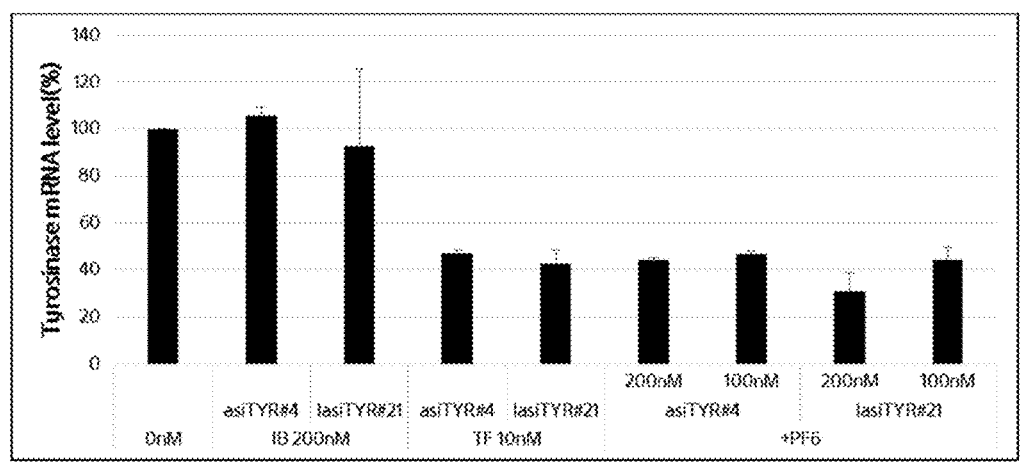
FIG. 11 shows the effect of treatment of MNT-1 cells with exemplary asiRNAs and lasiRNAs. Each complex identified was incubated with MNT-1 cells for 48 hours at the indicated concentration and tyrosinase mRNA expression was determined by real-time RT-PCR.

As seen in FIG. 11, MNT-1 cell lines treated with the PF6-complexed asiRNA or lasiRNA had significantly reduced levels of tyrosinase mRNA compared to control.

To test the treated MNT-1 cells for tyrosinase protein expression and melanin production, western blot and melanin content assays were performed as described above 48 hours after media replacement.

Figure 12:
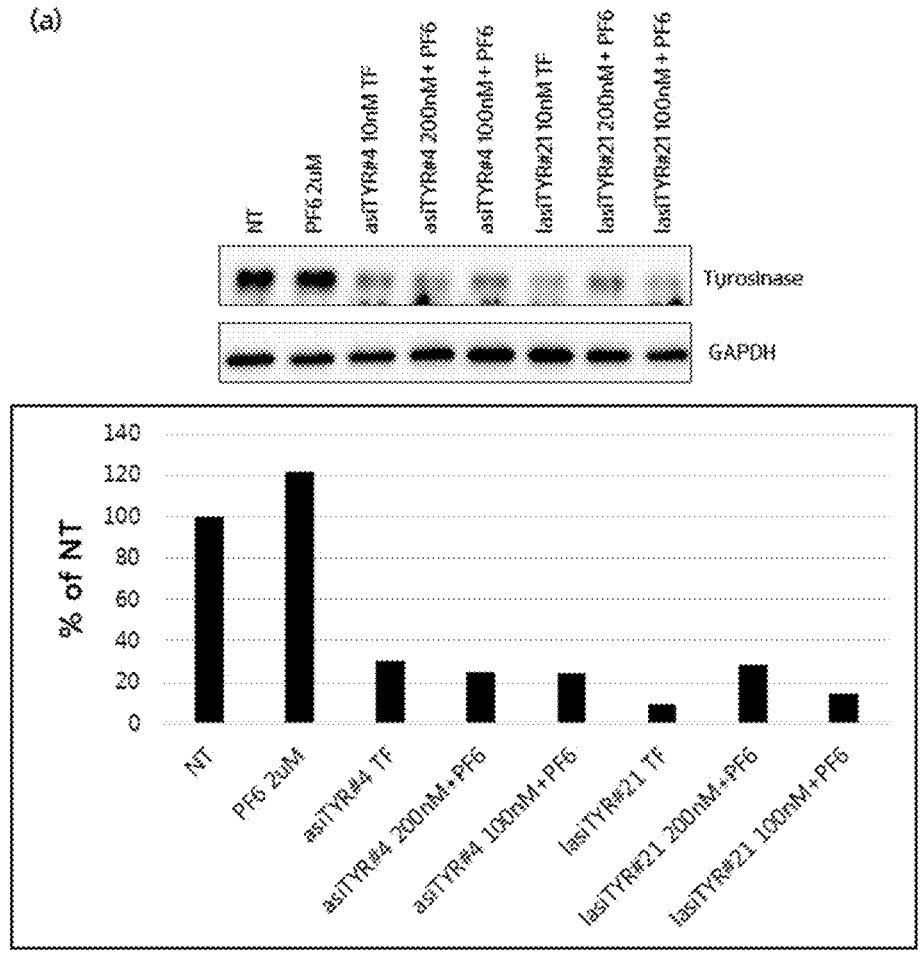
FIG. 12 shows the effect of treatment of MNT-1 cells with exemplary asiRNAs and lasiRNAs. Panel (a) depicts the results produced by a western blot for tyrosinase expression by MNT-1 cells 72 hours after the treatment with exemplary asiRNAs, lasiRNAs or controls. Panel (b) depicts the melanin content of MNT-1 cells 72 hours after treatment with exemplary asiRNAs, lasiRNAs or controls (NT=no treatment).
Figure 12:
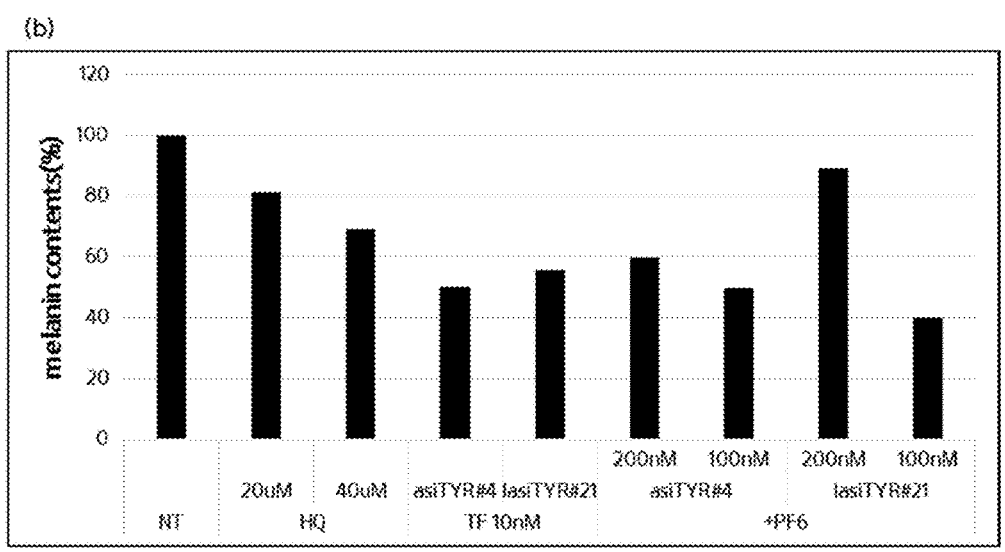

As seen in FIG. 12, cell lines treated with asiTYR(4)/PF6 complex and lasiTYR(21)/PF6 complex exhibited at least 70% tyrosinase protein inhibition compared to control. Additionally, cells treated with asiTYR(4)/PF6 complex and lasiTYR(21)/PF6 complex exhibited less melanin production than control.

Example 8: Inhibition of Melanin Synthesis in Reconstructed Skin Model Using an Exemplary cp-asiRNA Tyrosinase expression and melanin level was analyzed in an cp-asiTYR#4-1 treated 3-D skin model. MEL-300-B (MatTek), a reconstructed skin model, was used in this study. MEL-300-B was stabilized in EPI-100-NMM-113 media 24 hours before treatment with cp-asiTYR#4-1. For annealing, cp-asiTYR#4-1 dissolved in DEPC-treated water was incubated at 95° C. for 2 minutes and at 37° C. for 1 hour. MEL-300-B samples were treated with cp-asiTYR#4-1 every day for 13 days (final concentration=5 μM) by adding cp-asiTYR#4-1 directly to the media. As a control, other MEL-300-B samples were treated with kojic acid (Sigma, 2% final) as depicted in FIG. 14(a). The samples were harvested at day 14 and the melanocytes in the sample were analyzed using light microscopy. As seen in FIG. 14(c), cp-asiTYR#4-1 treatment reduced the level of melanocytes in the treated reconstructed skin model samples. Melanin level in each sample was analyzed using Fontana-Massons staining. As shown in FIG. 14(c), ci-asiTYR#4-1 treatment reduced the level of melanin in the treated reconstructed skin model samples.

In order to analyze mRNA level at day 14, samples were harvested in Isol-RNA lysis reagent (5PRIME) and homogenized by using a homogenizer (IKA). Total RNA from the each sample was extracted. For each sample, 500 ng of the extracted RNA was used for cDNA synthesis using the high-capacity cDNA reverse transcription kit (Applied Biosystems) according to the manufacturer's instructions. Quantitative real-time PCR was then performed using the StepOne real-time PCR system (Applied Biosystems). Amplification of the tyrosinase cDNA was detected using a power SYBR green PCR master Mix (Applied Biosystems). GAPDH was amplified as an internal control. As shown in FIG. 14(d), ci-asiTYR#4-1 treatment reduced the level of tyrosinase mRNA in the treated reconstructed skin model samples.

Protein level analysis was conducted as using western blot. Harvested samples in RIPA buffer (GE) were homogenized by using homogenizer (IKA) and protein from the each sample was obtained. Fifteen micrograms of the total protein extract were loaded onto a 12% SDS-PAGE gel and electrophoresed at 120 V. After electrophoresis, the proteins were transferred to PVDF membrane (Bio-rad) that had been previously activated with methanol (Merck) for 1 hour at 300 mA. The membrane was blocked for 1 hour at the room temperature with 5% skim milk (Seoul Milk) and then incubated overnight at 4° C. in 5% skim milk containing anti-tyrosinase antibody (Santa Cruz) and anti-β-actin antibody (Santa Cruz). The membrane was then washed three times with 1×TBST for 10 minutes and was incubated for 1 hour at the room temperature in 5% skim milk with HRP-conjugated secondary antibody. The membrane was washed with 1×TBST for 10 minutes and treated with 1×ECL (Thermo) for 1 minute. The tyrosinase and β-actin bands were then imaged using a Chemidoc instrument (Bio-rad). As shown in FIG. 14e, potent knockdown of tyrosinase protein was observed in the cp-asiTYR#4-1 treated reconstructed skin model sample.

To test melanin content, samples were harvested at day 14, lysed with RIPA buffer (GE) and centrifuged at 13000 rpm. The resulting pellet was dissolved in 100 μL of 1N NaOH (containing 10% DMSO) at 85° C. for 15 minutes and light absorption and melanin production were measured. As shown in FIG. 14(f), cp-asiTYR#4-1 treatment reduced melanin level in the treated reconstructed skin model samples.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An RNA complex comprising:
   an antisense strand of at least 19 nucleotides (nt) in length having sequence complementarity to a tyrosinase mRNA sequence and comprising a nucleotide sequence of SEQ ID NO: 8, SEQ ID NO: 18, SEQ ID NO: 20, SEQ ID NO: 32, SEQ ID NO: 90, or SEQ ID NO: 120; and
   a sense strand of 15 to 17 nt in length having sequence complementarity to the antisense strand and comprising a nucleotide sequence of SEQ ID NO: 7, SEQ ID NO: 17, SEQ ID NO: 19, SEQ ID NO: 31, SEQ ID NO: 89, or SEQ ID NO: 119,
   wherein the antisense strand and the sense strand form a complex in which the 5' end of the antisense strand and the 3' end of the sense strand form a blunt end.

2. The RNA complex of claim 1, wherein the antisense strand is 19 to 21 nt in length.

3. The RNA complex of claim 1, wherein the antisense strand is at least 24 nt in length.

4. The RNA complex of claim 3, wherein the antisense strand is 24 to 121 nt in length.

5. The RNA complex of claim 1, wherein the sense strand has a sequence of SEQ ID NO: 7 and the antisense strand has a sequence of SEQ ID NO: 8.

6. The RNA complex of claim 1, wherein the sense strand has a sequence of SEQ ID NO: 17 and the antisense strand has a sequence of SEQ ID NO: 18.

7. The RNA complex of claim 1, wherein the sense strand has a sequence of SEQ ID NO: 19 and the antisense strand has a sequence of SEQ ID NO: 20.

8. The RNA complex of claim 1, wherein the sense strand has a sequence of SEQ ID NO: 89 and the antisense strand has a sequence of SEQ ID NO: 90.

9. The RNA complex of claim 1, wherein the RNA complex comprises a chemical modification.

10. The RNA complex of claim 9, wherein the RNA complex comprises a phosphorothioate bond.

11. The RNA complex of claim 9, wherein the RNA complex is capable of penetrating the cellular membrane of a cell in the absence of a delivery vehicle.

12. A method of inhibiting tyrosinase expression by a cell comprising contacting the cell with an RNA complex of claim 1.

13. A method of inhibiting melanin production by a cell comprising contacting the cell with an RNA complex of claim 1.

14. A method of reducing melanin production in the skin of a subject comprising administering to the subject an RNA complex of claim 1.

15. The method of claim 14, wherein the subject has a skin pigmentation disorder associated with excessive melanin production, such as melasma or age spots.

16. The method of claim 14, further comprising administering to the subject a second skin lightening agent.

17. A method of treating a skin pigmentation disorder associated with excessive melanin production in a subject comprising administering to the subject an RNA complex of claim 1.

18. The method of claim 17, further comprising administering to the subject a second skin lightening agent.

19. A pharmaceutical composition comprising an RNA complex of claim 1 and a pharmaceutically acceptable carrier.

20. The pharmaceutical composition of claim 19, wherein the composition is formulated for topical delivery.

21. The pharmaceutical composition of claim 20, wherein the pharmaceutical composition is a cream or a lotion.

22. The pharmaceutical composition of claim 19, wherein the pharmaceutical composition further comprises a skin lightening agent.

23. A method of reducing melanin production in the skin of a subject comprising administering to the subject a pharmaceutical composition of claim 19.

24. A method of treating a skin pigmentation disorder associated with excessive melanin production in a subject comprising administering to the subject a pharmaceutical composition of claim 19.

25. The RNA complex of claim 5, wherein:
   (a) the sense strand is GCUGACAGGAGAUG*A*A*cholesterol; and
   (b) the antisense strand is UUCAUCUCCUGUCAGCU*U*C*U*G,
wherein * indicates a phosphorothioate bond.

* * * * *